United States Patent [19]
Slavin

[11] Patent Number: 5,843,435
[45] Date of Patent: Dec. 1, 1998

[54] IMMUNOTHERAPY OF CANCER WITH ALLOGENEIC LYMPHOCYTES

[75] Inventor: Shimon Slavin, Jerusalem, Israel

[73] Assignees: Hadasit Medical Research Services and Development Ltd., Israel; Baxter International Inc., Deerfield, Ill.

[21] Appl. No.: 714,144

[22] PCT Filed: Mar. 16, 1995

[86] PCT No.: PCT/US95/03303

§ 371 Date: Sep. 16, 1996

§ 102(e) Date: Sep. 16, 1996

[87] PCT Pub. No.: WO95/24910

PCT Pub. Date: Sep. 21, 1995

Related U.S. Application Data

[63] Continuation-in-part of Ser. No. 214,944, Mar. 17, 1994.

[51] Int. Cl.[6] .......................... A61K 38/21; A61K 45/05; A61K 39/395; A01N 63/00
[52] U.S. Cl. .................... 424/93.71; 424/93.7; 424/85.5; 424/85.7; 424/85.2; 424/85.4; 424/144.1
[58] Field of Search ................................ 424/85.2, 85.4, 424/144.1, 577, 578, 85.5, 85.7, 93.7, 93.71

[56] References Cited

U.S. PATENT DOCUMENTS

| | | | |
|---|---|---|---|
| 4,690,915 | 9/1987 | Rosenberg | 514/2 |
| 5,126,132 | 6/1992 | Rosenberg | 424/93 |

OTHER PUBLICATIONS

Slavin, S. et al., Cancer Investigation. 10(3): 221–227, 1992.
Slavin et al., Cellular–Mediated Immunotherapy of Leukemia in Conjunction with autologous and Allogeneic Bone Marrow Transplantation in Experimental Animals and Man. Blood 72(Suppl. 1): 407a (1988) (abstract).
Slavin et al., Cell–Mediated Cytokine–Activated (CCI) Immunotherapy of Malignant Hemotological Disorders for . . . chemotherapy of Bone Marrow Transplantation. Blood 76(Suppl.):2254a (1990) (abstract).
Slavin et al., Eradication of Minimal Residual Disease (MRD) Following Autologous (ABMT) and Allogeneic Bone Marrow Transplantation (BMT) by . . . in Experimental Animals and Man. Blood 80:535a (1992) (abstract).
Nagler et al., Adoptive Immunotherapy with Mismatched Allogeneic Peripheral Blood Lymphocytes (PBL) Following Autologous Bone Marrow Transplantation (ABMT). Exp. Hematol. 20: 705 (1992) (Abstract).
Slavin et al., Immunotherapy of Minimal Residual Disease in Conjunction With Autologous and Allogeneic Bone Marrow Transplantation (BMT). Leukemia (England) 6 (Suppl. 4):164–66 (1992).
Slavin et al., Immunotherapy of Minimal Residual Disease by Immunocompetent Lymphocytes and their activation by Cytokines. Cancer Invest. 10: 221–227 (1992).
Slavin et al., Induction of Cell–Mediated Il–2–Activated Antitumor Responses in Conjunction with Autologous and Allogeneic Bone Marrow Transplantation. Transplant. Proc. 23: 802–03 (1991).
Johnson et al., Delayed Infusion of Normal Donor Cells After MHC–Matched Bone Marrow Transplantation Provides an Antileukemia Reaction Without Graft–Versus–Host Disease. Bone Marrow Transplant. 11: 329–336 (1993).
Sykes et al., Achieving Alloengraftment Without Graft–Versus–Host Disease: Approaches Using Mixed Allogeneic Bone Marrow Transplantation. Bone Marrow Transplant. 3: 379–86 (1988).
Sykes et al., Interleukin 2 Prevents Graft–Versus–Host Disease While Preserving the Graft–Versus–Leukemia Effect of Allogeneic T Cells. Proc. Natl. Acad. Sci. USA 87: 5633–37 (1990).
Samuel et al., Effects of Interleukin 2 on Engraftment Following Autologous Bone Marrow Transplantation (ABMT) in Dogs. Leukemia Res. 16: 967–72 (1992).
Ackerstein et al., Use of Recombinant Human Interleukin–2 in Conjunction with Syngeneic Bone Marrow Transplantation in Mice as a Model for Control of Minimal Residual Disease . . . Blood 78: 1212–15 (1991).
Slavin et al., Induction of Cell–Mediated IL–2 Activated Antitumor Responses in Conjunction with Autologous and Allogeneic Bone Marrow Transplantation. Transplant. Proc. 23: 802–03 (1991).
Slavin et al., The Graft–Versus–Leukemia (GVL) Phenomenon: Is GVL Separable from GVHD? Bone Marrow Transplant. 6: 155–61 (1990).
Slavin et al., Il–2 Acivated Cell–Mediated Immunotherapy: Control of Minimal Residual Disease in Malignant Disorders by Allogeneic Lymphocytes and Il–2. Bone Marrow Transplant. 6 (Suppl. 1): 86–90 (1990).
Eckerstein et al., Immunotherapy in Conjunction with Autologous Bone Marrow Transplantation. Bone Marrow Transplant. 5 (Suppl. 1): 38 (1990).
Slavin et al., Toward Improvement of Therapeutic Strategies in Leukemia by Amplification of the Immune Response Against Leukemia. Haematol. and Blood Transfusion 13: 36–40 (1990).
Mule et al., The Anti–Tumor Efficacy of Lymphokine–Activated Killer Cells and Recombinant Interleukin 2 in Vivo. J. Immunol. 135: 1–7 (1985).

(List continued on next page.)

*Primary Examiner*—David Saunders
*Assistant Examiner*—F. Pierre VanderVegt
*Attorney, Agent, or Firm*—Mark J. Buonaiuto; Mark S. Ellinger

[57] ABSTRACT

Methods have been discovered for treating residual disease following removal of most or a substantial fraction of malignant cells from a cancer patient. An autologous stem cell transplant is performed on the patient. Following partial hematopoiesis recovery, the patient is infused with allogeneic peripheral blood lymphocytes, either alone or in combination with in vivo or in vitro T-cell activation. The infused allogeneic lymphocytes engender and antimalignant cell response.

22 Claims, 6 Drawing Sheets

OTHER PUBLICATIONS

Weiss et al., Use of Recombinant Human Interleukin–2 in Conjunction with Bone Marrow Transplantation as a Model for Control of Minimal . . . I. Treatment of Murine Leukemia Cancer Invest. 10: 19–26 (1992).

Rosenberg, S.A., Adoptive Immunotherapy of Cancer: Accomplishments and Prospects. Cancer Treatment reports 68: 233–55 (1984).

Mule et al., Adoptive Immunotherapy of Established Pulmonary Metastases with LAK Cells and Recombinant Interleukin–2. Science 225: 1487–89 (1984).

Slavin et al., New Therapeutic Strategies for Autologous and Allogeneic Bone Marrow Transplantation. Exp. Hematol. 15: 595 (1987).

Truitt and Atasoylu, Impact of Pretransplant Conditioning and Donor T Cells on Chimerism, Graft–Versus–Host Disease, Graft–Versus–Leukemia Reactivity, and Tolerance After Bone . . . Blood 77:2515–23 (1991).

Cheever et al., Augmentation of the Anti–Tumor Therapeutic Efficacy of Long–Term Cultured T Lymphocytes by In Vivo Administration of Purified Interleukin 2. J. Exp. Med. 155: 968–80 (1982).

Slavin, Autologous Stem Cell Transplantation at the National Bone Marrow Transplantation in Jerusalem, A Means for Accomplishing Maximal Tumor Cytoreduction and a Starting Point for Application of Immunotherapy at the Stage of Minimal Residual Disease, Autol. BMT Newsletter, 6:4–6 (1992).

Slavin et al., "Control of Relapse Due to Minimal Residual Disease (MRD) by Cell–Mediated Cytokine–Activated Immunotherapy in Conjunction With Bone Marrow Transplantation", Bailliere's Clin. Haematol., vol. 4, No. 3, pp. 715–725 (Jul. 1991).

Slavin et al., "New Developments in Bone Marrow Transplantation", Current Opinion in Oncology, 3:254–271 (1991).

Slavin, "New Developments in Bone Marrow Transplantation", Pediatric Immunology, vol. 3, pp. 48–65 (1993).

Slavin et al., New Animal Models for Control of Minimal Residual Disease (MRD) in the Treatment of Leukemia in Conjunction With Autologous and Allogeneic Bone Marrow Transplantation (BMT) Using Cell–Mediated Cytokine–Activated Immunotherapy (CCI). 8th International Congress of Immunology, Budapest 1992; p. 549 (Abstract).

IMMUNOTHERAPY OF CANCER WITH ALLOGENEIC LYMPHOCYTES

This application is a 371 of PCT/US95/03303, filed Mar. 16, 1995 and is a continuation in part of Ser. No. 08/214,944, filed Mar. 17, 1994.

FIELD OF THE INVENTION

This invention relates to methods of eradicating residual tumor cells following surgical intervention, chemotherapy and/or radiotherapy. The methods involve administration of allogeneic lymphocytes following autologous stem cell transplantation. More particularly, this invention relates to use of HLA-compatible or HLA-mismatched allogeneic lymphocytes to induce a graft-versus-malignant cell response following autologous stem cell transplantation.

BACKGROUND OF THE INVENTION

Patients with malignant hematological disorders resistant to conventional doses of chemotherapy and/or radiation may be treated by autologous or allogeneic bone marrow transplantation. Bone marrow transplantation (BMT) makes it possible to administer to patients with resistant disease high, "supralethal," combinations of chemotherapy and radiation, ignoring the irreversible toxicity of such therapeutic combinations on the normal bone marrow compartment. Nevertheless, such "debulking" of a patient's tumor(s) can leave a fraction of residual malignant cells that may lead to disease relapse. Several lines of evidence suggest that a significant proportion of the beneficial effect of allogeneic BMT (i.e., BMT from an individual not genetically identical to the host patient) stems from cell-mediated interactions of immune cells of donor origin against residual tumor cells in the host that have escaped the chemoradiotherapy debulking regimen.

Following allogeneic BMT, the incidence of relapse is significantly lower in leukemia patients with clinical manifestations of acute or chronic graft versus host disease (GVHD), as compared with patients with no GVHD, indicating that immune-mediated allogeneic interactions or immunocompetent cells of donor origin against the host are also accompanied by graft vs. leukemia (GVL) effects. Weiden et al., N. Engl. J. Med. 300: 1068 (1979); Weiden et al., N. Engl. J. Med. 304: 1529–33 (1981); Weiden et al., Transplantation 13: 248–51 (1981); Barrett et al., Blood 74: 862 (1989); Sullivan et al., Blood 73:1720 (1989); Horowitz et al., Blood 75: 555 (1990); Slavin et al., Bone Marrow Transplant. 6: 155–61 (1990).

Higher relapse rates seem to occur in patients undergoing allogeneic BMT with T-lymphocyte depletion for prevention of GVHD compared to recipients of non-T cell depleted marrow allografts, regardless of the severity of GVHD. Horowitz et al., Blood 75:555 (1990); Slavin et al., Bone Marrow Transplant. 6:155–61 (1990); Goldman et al., Ann. Inter. Med. 108: 806–14 (1988); Ringden and Horowitz, Transplant. Proc. 21: 2989–92 (1989); Goldman et al., Ann. Int. Med. 108: 806 (1988). Likewise, relapse rates in patients with acute leukemia or chronic myeloid leukemia reconstituted by bone marrow grafts obtained from an identical twin (syngeneic grafts) are significantly higher than in those reconstituted by bone marrow cells obtained from an HLA-identical but non-syngeneic sibling. Ringden and Horowitz, Transplant. Proc. 21: 2989–92 (1989). Similarly, relapse rates following transplantation of the patient's own (autologous) marrow, even following adequate purging in vitro for elimination of residual leukemia cells, are significantly higher than following allogeneic BMT. Armitage, Curr. Opinion in Hematol. 1993: 240–45 (1993). Thus, the less-than optimal results with autologous BMT (ABMT) are similar to the results seen with syngeneic marrow transplantation. All of the above data suggests that in practical terms GVHD or GVHD-potential correlates with a lower incidence of relapse.

Allogeneic donor cells may also play a role against lymphoma, as shown in experimental animals, Slavin et al., Cancer Immunol. Immunother. 11: 155–58 (1981), and humans. Phillips et al., J. Clin. Oncol. 4: 480–88 (1986); Ernst et al., Proc. of the 4th International Conference on Lymphoma, Lugano 1990, Abstract #P35; Chopra et al., J. Clin. Oncol. 10: 1690–95 (1992). As shown in experimental animals, graft-versus-tumor effects (GVT), similar to graft versus-leukemia effects (GVL), may occur following BMT, independently of GVHD. Moscovitch and Slavin, J. Immunol. 132: 997–1000 (1984). As used herein, GVL is one form of GVT.

Although GVHD-associated anti-leukemia effector mechanisms may be of benefit in BMT, nevertheless GVHD represents one of the major obstacles in allogeneic BMT, even among perfectly HLA-matched siblings. Acute GVHD develops in the majority of recipients of allogeneic BMT, with clinically significant manifestations in 26–64% of the recipients despite optimal post-transplant immunosuppressive prophylaxis. Storb et al., Blood 73: 1729 (1989). Chronic GVHD may occur in up to 45% of long term survivors. Storb et al., Blood 73: 1729 (1989). There is no satisfactory therapy for patients with established GVHD and hence patients with severe manifestations of acute or chronic forms of the disease are prone to develop multisystem complications that may require frequent hospitalizations, leading to poor quality of life and occasionally serious or even fatal complications.

GVHD following allogeneic BMT can be prevented by adequate pretransplant T-lymphocyte depletion, using no post-transplant anti-GVHD prophylaxis. Reisner et al., In: Slavin, S(ed.), Tolerance in Bone Marrow and Organ Transplantation. Elsevier, Amsterdam (1984), p. 293; Waldmann et al., Lancet 2: 483–85 (1984); Slavin et al., Transplant. Proc. 17: 465–67 (1985). BMT without GVHD represents a better tolerated procedure that may necessitate shorter hospitalization with superior subjective immediate outcome following allogeneic BMT. In addition, the quality of life of long-term survivors without GVHD is clearly better than for those patients with severe acute or chronic GVHD.

Unfortunately, the advantages of GVHD-free-allogeneic BMT are counterbalanced by other serious complications due to untoward effects of T-lymphocyte depletion, such as increased incidence of graft rejection, occurring in 10–30% of recipients, as well as increased rates of tumor relapse. Martin et al., Bone Marrow Transplant. 3: 445 (1988); Kernan et al., Transplantation 43: 842 (1987); Waldmann et al., Lancet 2: 483–85 (1984); Slavin et al., Transplant. Proc. 17: 465–67 (1985). Consequently, there seems to be no clear evidence to date for a significant overall benefit of GVHD prevention by T-lymphocyte depletion.

Clearly, it would be a significant advance in the art to be able to combine the benefits of minimal or controllable GVHD risk following ABMT or autologous stem cell transplantation (ASCT) with induction of graft-versus-malignant cell response that may be associated with GVHD following allogeneic BMT.

SUMMARY OF THE INVENTION

The present invention includes a method of treating a human cancer patient who has undergone a malignant cell debulking procedure in which autologous stem cell transplantation has been performed incident to the debulking procedure. In other words, the patient's own stem cells were infused back into the patient in order to reconstitute the patient's bone marrow following the tumor debulking. Generally the patient is considered to be at risk for disease relapse due to a population of residual malignant cells that may remain viable in the patient following the debulking procedure. The patient is monitored until the patient is partially hematopoiesis recovered but is not fully immune-reconstituted. Then, the patient is administered allogeneic lymphocytes in a regimen that causes a clinically significant graft-versus-malignant cell response. Allogeneic lymphocytes in this setting are lymphocytes taken from an individual not genetically identical to the patient into which the lymphocytes are infused. The patient is monitored for levels of malignant cells deriving from any residual malignant cells that might have been present following the original debulking procedure. This monitoring may constitute one or more molecular or cellular assays to detect or quantify malignant cells, may constitute a monitoring program to detect clinical signs of relapse, or any combination of these monitoring methods.

At used herein, a clinically significant response permits, for example, the patient to avoid relapse, substantially prolongs the time to relapse or otherwise engenders a beneficial condition that significantly prolongs life. Thus, evidence for a clinically significant response may include, for example, absence or delay of relapse, induction of temporary or permanent remission, evidence for elimination of minimal residual disease, i.e., elimination of disease-specific markers and, where appropriate, elimination of markers directed to host-specific cells.

In situations where allogeneic lymphocytes are not selected (see below) to reduce or eliminate the GVHD potential of the cells, it is preferable that HLA-compatible allogeneic lymphocytes are used. A regimen utilizing HLA-compatible allogeneic lymphocytes may comprise the following steps in sequence:

a) treating the patient by administration (e.g., infusion) of about $10^7$ cells/kg to about $10^9$ cells/kg of HLA-compatible lymphocytes;

b) monitoring the patient for indications of a graft-versus-malignant cell response; and c) if no or insufficient graft-versus-malignant cell response develops in the patient, escalating the treatment by performing at least one of the following procedures: (1) administration of a number of HLA-compatible, allogeneic lymphocytes greater than the number of lymphocytes administered in step (a); (2) administration of a number of HLA-compatible, allogeneic lymphocytes at least as great as the number of lymphocytes administered in step (a), accompanied by in vivo administration of at least one T-cell activator to the patient; (3) administration of HLA-compatible, allogeneic activated donor lymphocytes (ADL) to the patient; and (4) administration of HLA-compatible, allogeneic ADL, accompanied by administration in vivo of at least one T-cell activator to the patient. More than one of these procedures can be performed if no or insufficient graft-versus-malignant cell response develops in the patient following the first or subsequent procedure.

In an alternative embodiment, step (a) above can be augmented by administering, concomitant with the allogeneic lymphocytes, at least one T-cell activator to the patient. Since the T-cell activator is administered directly to the patient, the infused allogeneic lymphocytes are exposed to the activator in vivo.

The present invention also includes an alternative method of treating a human cancer patient in which GVHD is used as a clinical marker. Following malignant cell debulking and autologous stem cell transplantation, the patient is monitored until the patient is partially hematopoiesis recovered but is not fully immune-reconstituted. Then, the patient is administered HLA-compatible, allogeneic lymphocytes in a regimen that causes a mild graft-versus-host response. The patient is then monitored, as above, for levels of malignant cells deriving from any residual malignant cells that might have been present following the original debulking procedure.

As used herein, the term "graft-versus-host response" includes but is not limited to the classic clinical symptoms of graft-versus host disease (GVHD), known to those having ordinary skill in the art. Patients with a mild graft-versus-host response include those with, for example, Grade I or Grade I/II cutaneous GVHD or other forms of GVHD that stop short of severe manifestations leading to serious or fatal multisystem complications. A mild graft-versus-host response could also include molecular or cellular responses that correlate with the clinical symptoms of GVHD or with the impending onset of the clinical symptoms of GVHD.

For the above-described alternative method involving mild GVHD, the regimen for administration of HLA-compatible lymphocytes may comprise the following steps in sequence:

a) treating the patient by administration of about $10^7$ cells/kg to about $10^9$ cells/kg of HLA-compatible, allogeneic lymphocytes;

b) monitoring the patient for indications of a mild graft-versus-host response; and c) if no or insufficient graft-versus-host response develops in the patient, escalating the treatment by performing at least one of the following procedures: (1) administration of a number of HLA-compatible, allogeneic lymphocytes greater than the number of lymphocytes administered in step (a); (2) administration of a number of HLA-compatible, allogeneic lymphocytes at least as great as the number of lymphocytes administered in step (a), accompanied by in vivo administration of at least one T-cell activator to the patient; (3) administration of HLA-compatible, allogeneic ADL to said patient; and (4) administration of HLA-compatible, allogeneic ADL, accompanied by administration in vivo of at least one T-cell activator to the patient. More than one of these procedures can be performed if no or insufficient graft-versus-host response develops in the patient following the first or subsequent procedure.

In an alternative embodiment, step (a) above can be augmented by administering, concomitant with the allogeneic lymphocytes, at least one T-cell activator to the patient. Since the T-cell activator is administered directly to the patient, the infused allogeneic lymphocytes are exposed to the activator in vivo.

In a further alternative embodiment involving mild GVHD, the regimen for administration of HLA-compatible lymphocytes may comprise the following steps in sequence:

a) administering to the patient about $10^7$ cells/kg to about $10^9$ cells/kg of HLA-compatible, allogeneic lymphocytes and at least one T-cell activator to the patient;

b) monitoring the patient for signs of a mild graft-versus-host response;

c) if no or insufficient graft-versus-host response develops in the patient, administering about $10^7$ cells/kg to about $10^9$ cells/kg of HLA-compatible, allogeneic ADL and at least one T-cell activator to the patient;

d) monitoring the patient for signs of a mild graft-versus-host response;

Alternatively, the ADL may be given in the initial infusion. In this case the regimen for administration of HLA-compatible lymphocytes may comprise the following steps in sequence:

a) administering to the patient of about $10^5$ cells/kg to about $10^9$ cells/kg of HLA-compatible, allogeneic lymphocytes in which at least some of the HLA-compatible, allogeneic lymphocytes are ADL, together with a T-cell activator, to the patient;

b) monitoring the patient for signs of a mild graft-versus-host response;

c) if no or insufficient graft-versus-host response develops in the patient, administering about $10^5$ cells/kg to about $10^9$ cells/kg of HLA-compatible, allogeneic ADL and at least one T-cell-activator to the patient;

d) monitoring the patient for signs of mild graft-versus-host response;

In any of the methods described herein, the T-cell activator can be any suitable agent that activates the T-cell signal transduction pathway leading to lymphocyte activation. Lymphocyte activation involves a series of interrelated events described, for example, in Abbas et al., *Cellular and Molecular Immunology, Second Edition*, W. B. Saunders Co. (1994), pages 153–65. A T-cell activator may comprise, without limitation, any one or more of the following: interleukin 1 (IL1), interleukin 2 (IL2), interleukin 4 (IL4), interleukin 5 (IL5), interleukin 6 (IL6), interleukin 7 (IL7), interleukin 12 (IL12), interleukin 13 (IL13), interferon alpha (IFNα), interferon gamma (IFNγ), tumor necrosis factor (TNFα), an anti-CD3 antibody or antigen-binding fragments thereof (anti-CD3), an anti-CD28 antibody or antigen-binding fragments thereof (anti-CD28), phytohemagglutinin, concanavalin-A and phorbol esters. Any of these activators can be a native factor obtained from natural sources, a factor produced by recombinant DNA methodology, a chemically synthesized polypeptide or other molecule, or any derivative having the functional activity of the native factor.

The stem cells used for autologous stem cell transplantation may be obtained from bone marrow, from the peripheral circulation, or, where appropriate, from fetal sources such as fetal tissue, fetal circulation and umbilical cord blood. Cancer patients treatable with the methods of the present invention are any patients having a pathological condition caused by malignant cells, including without limitation leukemia, lymphoma, and breast cancer.

In an alternative embodiment, the allogeneic lymphocytes administered to the patient in the various methods of the present invention may be selected to have a substantially diminished graft-versus-host activity compared to unselected lymphocytes. Preferably the selected lymphocytes are CD8+ lymphocytes. In cases where selected lymphocytes having substantially diminished graft-versus-host activity are used, the lymphocytes may be either HLA compatible or HLA-mismatched with the patient. In an initial infusion of HLA-mismatched lymphocytes, for example HLA-mismatched CD8+lymphocytes, as few as about $10^5$ to as many as about $10^9$ cells may be administered.

The present invention also includes the use of a T-cell activator in the manufacture of a medicament for the treatment of a human cancer patient, where the patient has undergone a malignant cell debulking procedure and has further undergone autologous stem cell transplantation incident to the debulking procedure. As above, the patient is at risk for disease relapse due to a population of residual malignant cells that may remain viable in the patient following the debulking procedure. The treatment of this patient involves one or more of the Allo-CMI and/or Allo-CCI methods of the invention described above.

The invention further includes the use of allogeneic lymphocytes (i.e., allogeneic to a patient to be treated) in the manufacture of a medicament for the treatment of a human cancer patient, where the patient has undergone a malignant cell debulking procedure and has further undergone autologous stem cell transplantation incident to the debulking procedure. As above, the patient is at risk for disease relapse due to a population of residual malignant cells that may remain viable in the patient following the debulking procedure. The treatment of this patient involves one or more of the Allo-CMI and/or Allo-CCI methods of the invention described above.

The present invention further includes an article of manufacture comprising packaging material and a container within the packaging material. The packaging material contains a label or package insert indicating that the contents of the packaging material may be used in any of the above-described methods of the invention for treating a human cancer patient. Preferably a container included in the packaging material is a collapsible container (e.g., a plastic bag) comprising opposing walls of flexible material and a flexible tube (e.g., a plastic tube) protruding from the container. A T-cell activator may be contained within the container. Preferably the tube is adapted to receive allogeneic lymphocytes (i.e., allogeneic to a patient to be treated) into the container. If T-cell activator is present in the container, the in-coming lymphocytes become activated. These ADL then can be used to treat a cancer patient according to the methods of the invention described above.

DETAILED DESCRIPTION OF THE INVENTION

Figure 1:
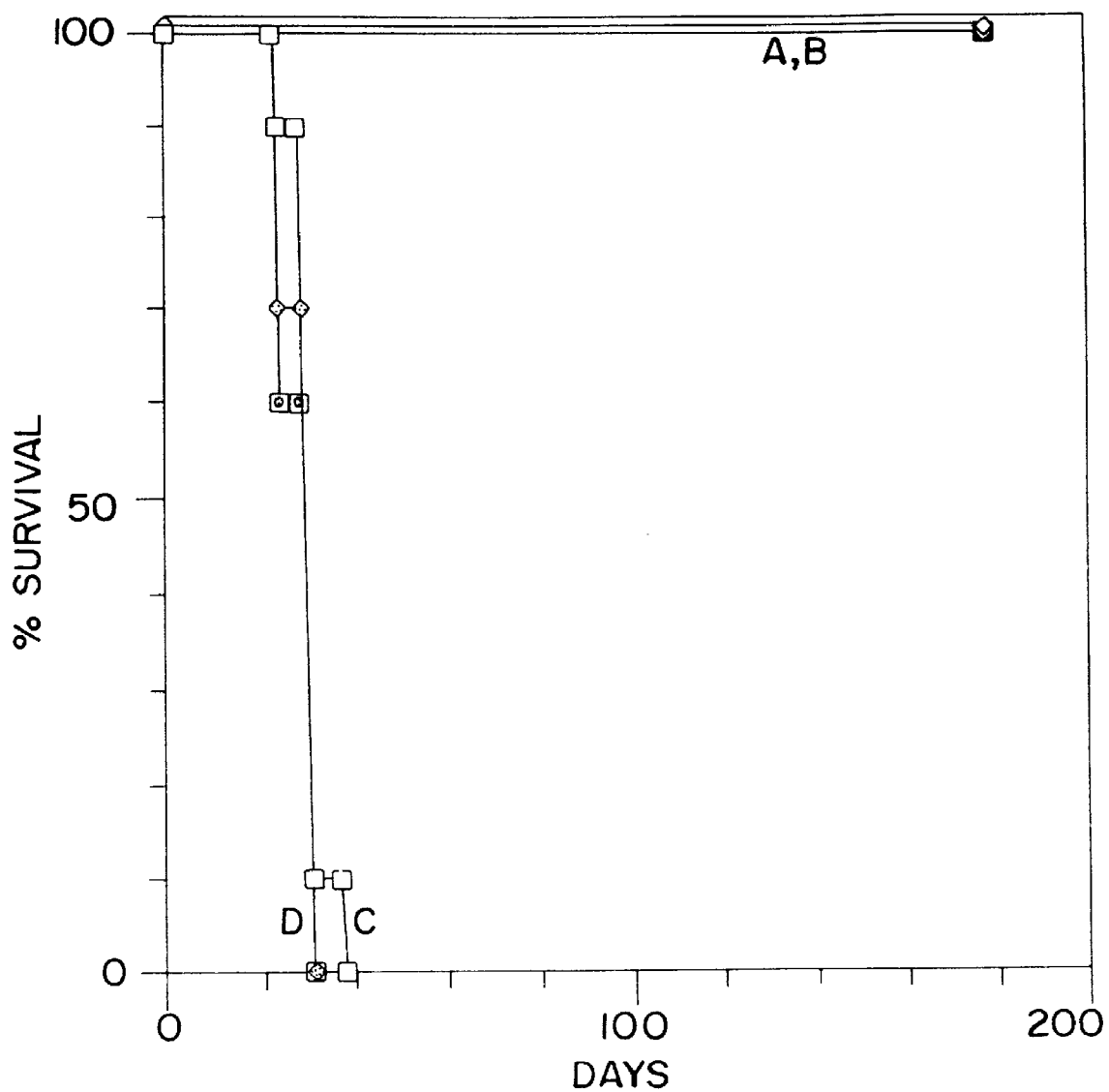
FIG. 1 depicts the results of adoptive transfer of spleen cells obtained from lethally irradiated F1 mice transplanted with $10^7$ syngeneic bone marrow cells and $10^5$ BCL1 cells in addition to $20–30\times10^6$ PBL from allogeneic mice with (A, n=40) or without (B, n=40) concomitant in vivo rhIL2 treatment ($12\times10^4$ IU×2/day for 5 days IP). A similar group received syngeneic (F1) PBL given with (C, n=20) or without (D, n=20) rhIL2. A control group had adoptive transfer to spleen cells obtained from 10 untreated F1 recipients (E, n=20).

The present inventor has employed allogeneic peripheral blood lymphocytes, alone or in combination with T-cell activator treatment in vivo or in vitro, for successful elimination of minimal residual disease following chemotherapy and/or radiotherapy. Appropriate treatment regimens have been circumscribed by studies in laboratory animals, and the treatment protocols have been further extended to human patients at high risk for disease relapse.

A spontaneous, transplantable murine B-cell leukemia/lymphoma of BALB origin (BCL1) was used to investigate elimination of minimal residual disease (MRD) following bone marrow transplantation. As used herein, MRD refers to a condition wherein residual malignant cells remain viable in a patient following a primary and/or metastatic tumor "debulking" procedure. The debulking procedure may comprise any protocol that removes or destroys tumor cells, including without limitation surgical excision, chemotherapy or radiotherapy, or any combination of these approaches. Such treatment removes a significant fraction of malignant cells from the patient, but may leave a clinically significant number of residual malignant cells that put the patient at risk of relapse. The term "tumor" as used herein includes all pathological conditions involving malignant cells; this can include "solid" tumors arising in solid tissues or organs as well as "liquid" tumors such as leukemias and lymphomas deriving from malignant transformation of hematopoietic cells.

In autologous bone marrow transplantation (ABMT) with human patients, an individual receives his or her own bone marrow cells by infusion following a tumor debulking procedure. Generally, the bone marrow cells are taken from the patient and preserved, for example by cryopreservation, prior to the debulking procedure. ABMT permits an otherwise lethal debulking regimen to be employed, e.g., chemotherapy or radiotherapy that severely damages or destroys the patient's bone marrow. Following the debulking procedure, the patient's bone marrow is reconstituted by stem cells present in the preserved sample of bone marrow.

Stem cells capable of reconstituting a patient's immune system can be obtained not only by direct extraction from the bone marrow, but also from the patient's peripheral circulation following mobilization of such cells from the bone marrow. This can be accomplished by treatment of the patient with granulocyte colony stimulating factor (G-CSF) or other appropriate factors that induce movement of stem cells from the bone marrow into the peripheral circulation. Following mobilization, the stem cells can be collected from peripheral blood by any appropriate cell apheresis technique, for example through use of a commercially available blood cell collection device as exemplified by the CS 3000® Plus blood cell collection device marketed by the Fenwal Division of Baxter Healthcare Corporation. Methods for performing apheresis with the CS 3000® Plus machine are described in Williams et al., Bone Marrow Transplantation 5: 129–33 (1990) and Hillyer et al., Transfusion 33: 316–21 (1993), both publications being incorporated herein by reference. Stem cells collected from the peripheral blood are termed herein "peripheral blood stem cells" (PBSC). The term "autologous stem cell transplantation" (ASCT) is used herein to refer to any infusion into a patient of that same patient's stem cells, derived from any appropriate source (e.g., bone marrow or peripheral circulation). As such, ABMT, where the autologous infused cells are extracted directly from the bone marrow of the patient, may be considered simply one form of ASCT.

It is possible to create an experimental regime in mice that simulates ASCT in humans. This is done through use of stem cell donors and recipients derived from a syngeneic strain of mice. In such strains, inbreeding has created a situation in which, for practical purposes, mice within the strain are genetically identical to each other. Such mice accept tissues and organs transplanted between individuals without evidence of immune rejection, in a manner analogous to acceptance of a patient's own cells following ASCT. Transplantation of bone marrow-derived stem cells between such mice is referred to herein as "syngeneic bone marrow transplantation" (SBMT) and may be considered analogous to ABMT and ASCT in humans.

In the present experiments, mice received a lethal dose of total body irradiation (TBI) or, alternatively, a lethal dose of cyclophosphamide administered intraperitoneally. Bone marrow cells (BMC) were extracted directly from the bone marrow of syngeneic mice. In some cases, these BMC preparations were treated with mafosfamide (ASTA-Z) to simulate a "purging" procedure in which the patient's stem cells, prior to ASCT, are treated to remove or destroy at least a fraction of any contaminating malignant cells. One day after irradiation or treatment with cyclophosphamide, the mice received $10^7$ syngeneic bone marrow cells by infusion into the lateral tail vein. To simulate MRD, $10^5$ BCL1 tumor cells were added to the syngeneic BMC prior to SBMT.

Following SBMT, recipient mice received either allogeneic cell-mediated immunotherapy (Allo-CMI) or allogeneic cell-mediated cytokine-activated immunotherapy (Allo-CCI). Allo-CMI involved transfer of immunocompetent allogeneic lymphocytes (i.e., lymphocytes from a mouse strain other than that of the recipient mice) at various times and at various doses, administered post-SBMT. Generally these lymphocytes represented peripheral blood lymphocytes (PBL) or mixtures of donor spleen and lymph node cells. Allo-CCI involved transfer of allogeneic lymphocytes pre-activated in vitro with recombinant human interleukin 2 (rhIL2). As used herein, the term "ADL" refers to such "activated donor lymphocytes," i.e., lymphocytes (human or mouse) activated in vitro with a T-cell activator such as rhIL2. In some experimental protocols, the Allo-CMI or Allo-CCI regimen was accompanied by simultaneous in vivo administration of rhIL2 to the recipient mice, in order to facilitate additional activation of the infused lymphocytes in vivo.

Failure to develop leukemia in primary recipients does not prove elimination of all BCL1 cells, since active suppression of existing tumor cells can prevent development of overt disease in these animals. This has been documented following allogeneic BMT and rhIL2 therapy. Slavin et al., Cancer Immunol. Immunother. 11:155 (1981); Slavin et al., Nat. Immun. Cell Growth Regul. 7:180 (1988). To establish conclusive evidence for eradication of residual malignant cells, spleen cells from the treated, or recipient, mice were adoptively transferred to secondary syngeneic recipients. If these secondary recipients failed to develop leukemia, it was judged that the original Allo-CMI- or Allo-CCI-treated mice were free of viable malignant cells, since as few as 1–10 cells have been shown to be capable of causing disease. Slavin et al., Cancer Res. 41:4162 (1981); Cohen et al., J. Immunol. 151: 4803–10 (1993).

The results of the SBMT experiments with mice suggested that effective immunotherapy of MRD can be achieved in vivo by cell therapy with alloreactive lymphocytes through an effect that can be further enhanced in vivo with a short course of intermediate-dose rhIL2. GVL-like effects were also induced by infusion of ADL without causing any gross impairment of the hematopoietic capacity of BMC in lethally irradiated recipients. Moreover, GVL effects induced by allogeneic lymphocytes as well as ADL could be further enhanced by concomitant rhIL2 therapy in vivo, most likely due to continuous in vivo activation of allogeneic effector cells against residual host malignant cells.

The data further indicate that eradication of BCL1 can be accomplished before overt clinical manifestations of GVHD in the primary recipients would have occurred, since experiments showed that GVL-like effects against BCL1 cells were achieved within 1–2 weeks following administration of allogeneic lymphocytes. This implies that temporary engraftment of allogeneic effector cells may be sufficient to induce beneficial GVL effects against MRD, without the need for permanent residence of allogeneic effector cells, which may put the patient at risk for severe GVHD across major histocompatibility barriers. Moreover, as the time interval between ASCT and the Allo-CMI/CCI treatment increases, larger numbers of donor's PBL can be administered with less likelihood of severe GVHD. Slavin et al., J. Exp. Med. 147:963 (1978); Slavin et al., Blood 80:535a (1992).

As such, it is preferred that an Allo-CMI or Allo-CCI regimen is begun only after the patient is partially hematopoieses recovered following the original tumor debulking procedure/ASCT. This raises the likelihood that the allogeneic inoculum will be rejected by reconstituting host immune cells in due time, after GVT (e.g., GVL) effects have been accomplished. On the other hand, it is also preferred that the Allo-CMI/Allo-CCI regimen is undertaken prior to full immune reconstitution of the patient, since the likelihood of premature rejection of the allogeneic inoculum, prior to beneficial GVL/GVT effects, is thereby reduced. Since full immune reconstitution following ASCT in humans frequently requires up to one year, the patient can be monitored until a stable clinical condition (e.g., condition of stabilized blood counts) is attained, as indicated by acceptable levels of, for example, white blood cells (WBC), hemoglobin (Hb) and platelets. This condition of partial hematopoieses recovery may be achieved beginning in a matter of weeks following ASCT in humans, well before full immune reconstitution diminishes the likelihood of successful Allo-CMI and/or Allo-CCI.

The Allo-CMI and Allo-CCI strategies developed in mice have been adapted to human patients in a variety of protocols undertaken by the present inventor in treating cancer patients at high risk of disease relapse. Cancer patients having acute myelogenous leukemia, chronic myelogenous leukemia, non-Hodgkin's lymphoma and metastatic breast cancer have been treated with the methods of the present invention.

Two of the earlier-treated patients with acute myelogenous leukemia were given relatively low numbers (e.g., about $10^4$ cell/kg) of allogenic peripheral blood lymphocytes as a first dose, in an effort to minimize the risk of serious GVHD. Thereafter, the patients were given escalating numbers of allogeneic peripheral blood lymphocytes at various time intervals to increase the chances of clinically significant graft-versus malignant cell response. Both of these early patients (patients 1 and 2 in Example 2, set out below) relapsed and died. Following this result, it was apparent that administration of graded increments of PBL, beginning with relatively low numbers, may not be effective.

In hindsight, it can be hypothesized that the initial low dose of allogeneic PBL produced only immunization without significant GVHD or graft-versus-malignant cell response. Thus, later, higher doses of allogeneic PBL, which otherwise might be effective, may have been promptly rejected by the patient and rendered ineffectual for graft-versus-malignant cell activity. Therefore, in subsequent cases, more cells (e.g., at least about $10^7$ cells/kg) were administered in the initial dose. With this initial higher dose of allogeneic cells following ASCT, satisfactory results have been obtained in many patients within the treatment population to date.

If human leukocyte antigen (HLA)-compatible allogeneic lymphocytes are used in the present procedures, such cells preferably are fully HLA-matched with the patient. Alternatively, HLA-compatible allogeneic cells may be at least haploidentical with the patient. Thus, if the allogeneic cells are derived from a sibling of the patient, some mismatch may be tolerated. For example, the HLA-compatible allogeneic cells may, in some cases, be single HLA locus-mismatched as demonstrated by Patient No. 12 described in EXAMPLE 2 below. If the allogeneic cells are derived from an unrelated individual, preferably the cells are fully HLA matched with the patient.

In a preferred embodiment of the present invention, an initial dose of at least about $10^7$ HLA-compatible allogeneic lymphocytes/kg is given once the patient has achieved a clinically stable condition (e.g., stabilized blood counts), i.e., once the patient is partially hematopoiesis recovered. Preferably, the patient is also administered T-cell activator in vivo, concomitant with administration of the HLA-compatible lymphocytes. Preferably the T-cell activator is human interleukin 2 produced through recombinant DNA technology (rhIL2) at a dose of about $6 \times 10^6$ IU of rhIL2/$m^2$/day, by subcutaneous injection, beginning on the same day as infusion of the allogeneic lymphocytes. Other appropriate T-cell signal transduction activators as set out above may be used, either with or without rhIL2, as long as the desired activation in vitro is obtained.

If GVHD fails to develop in a patient given the above-described numbers of HLA-compatible allogeneic lymphocytes with concomitant in vivo T-cell activator, then the treatment regimen is escalated. Preferably this is done by administering a second dose of allogeneic HLA-compatible lymphocytes preactivated in vitro with T-cell activator. Preferably the T-cell activator is a cytokine such as rhIL2, although, again, other T-cell signal transduction activators may be used either with or without rHIL2.

Prior to administration of the second dose of cells comprising ADL, and contingent on the particular status of an individual patient, cyclophosphamide (Cytoxan) or other appropriate immunosuppressants may be administered to the patient to avoid rejection of the second dose of cells. That is, the immunosuppressant is given in a dose effective for killing or inactivating host T cells that might otherwise operate to reject the second allogeneic inoculum; the immunosuppressant may have the added benefit of eliminating potential host suppressor cell functions that can interfere with the GVT effects of the infused ADL. Preferably, in vivo T-cell activator is administered to the patient concomitant with the second dose of allogeneic cells.

Although the above-described preferred embodiment is presently recommended, it is to be understood that any combination of allogeneic lymphocytes, in vivo T-cell activator and/or ADL is covered by the present invention, so long as the initial dose of cells corresponds to a number of HLA-compatible allogeneic lymphocytes that elicits a host response beyond mere immunization to a second dose of cells from the same or similar donor. Generally, this initial dose is at least about $10^7$ allogeneic peripheral blood lymphocytes/kg. However, it is possible that a lower dose of cells, e.g., about $10^5$ cells/kg, could be used if, for example, ADL were used in the initial infusion.

Between the Allo-CMI/CCI treatments or at the conclusion of an Allo-CMI/CCI regimen, the patient may be monitored for levels of malignant cells, i.e., for evidence of minimal residual disease. Such monitoring may comprise patient follow-up for clinical signs of relapse. The monitoring may also include, where appropriate, various molecular or cellular assays to detect or quantify any residual malignant cells. For example, in cases of sex-mismatched donors and recipients, residual host-derived cells may be detected through use of appropriate sex markers such as Y chromosome-specific nucleic acid primers or probes. In cases of single HLA locus mismatches between donors and recipients, residual host cells may be documented by polymerase chain reaction (PCR) analysis of Class I or Class II loci that differ between the donor and recipient. Alternatively, appropriate molecular markers specific for tumor cells can be employed. For example, nucleic acid primers and/or probes specific for the bcr/abl translocation in chronic myelogenous leukemia, for other oncogenes active in various tumors, for inactivated tumor suppressor genes, other tumor-specific genes, or any other assay reagents known to be specific for tumor cells, may be employed. Any of these or functionally comparable procedures may be used to monitor the patient for evidence or residual malignant cells.

Under normal circumstances, recipients of autologous or allogeneic bone marrow transplants receive only irradiated blood products when such products are required by the patient. These products are irradiated in order to avoid the possibility of engraftment of immunocompetent T-lymphocytes derived from the donor's blood product (e.g., platelets or red blood cells). In most institutions, irradiated blood products are also used for patients receiving high dose conventional chemotherapy without transplant, e.g., blood products given following induction of remission in leukemia and lymphoma patients. obviously, the chances for engraftment of immunocompetent T-lymphocytes from otherwise mismatched blood products is relatively small under normal circumstances. However, if immunosuppression is sufficient to permit engraftment, GVHD can be "stormy" and lethal.

In one embodiment of the present invention, described above, non-irradiated donor-type lymphocytes are used intentionally for induction of graft-versus-malignant cell effects. The method is structured to produce transient engraftment, so as to induce graft-versus-malignant cell effects that may be accompanied by mild GVHD. Since the donor cells used in this embodiment are HLA-compatible with the recipient, chances of engraftment are better than if the donor's cells were not functionally matched with the patient's major histocompatibility complex. Moreover, the chances of immediate rejection on the one hand and lethal GVHD on the other hand are relatively small because of the HLA compatibility. As such, the Allo-CMI/CCI protocols of this embodiment provide the possibility for transient engraftment of donor's PBL with effective GVT and with a minimal chance for induction of severe GVHD.

In alternative embodiments, T-cell subsets may be selected that retain GVT activity but that have a reduced or absent capability for inducing GVHD. In these embodiments, the use of HLA-compatible allogeneic lymphocytes is not required. Thus, although it may be desirable in some circumstances to used HLA-compatible lymphocytes, in other cases it is permissible to have a mismatch at two or more loci (HLA-mismatched lymphocytes). This is because the use of T-cell subsets with limited GVHD potential allows GHVD to be minimized even if the infused lymphocytes are not HLA compatible with the patient. In fact, GVT potential is enhanced through use of HLA mismatched allogeneic lymphocytes.

For selection of an appropriate T-cell subset, the present inventor has established that CD8+ T lymphocytes represent the effector cells of the GVT response. Experiments establishing this finding are set out in EXAMPLE 4 below. The ability of CD8+ cells to induce GVHD is reduced compared to unselected T cells. As such, CD8+ cells represent a useful T-cell subset for use in the clinical setting, since the risk of GVHD is diminished while significant GVT activity is retained. The term "selected" as used herein means use of any procedure that provides a T-cell population relatively enriched for a desired T-cell subset. This could include, for example, positive selection for CD8+ cells, or elimination or reduction of CD4+ cells leaving a population correspondingly enriched for CD8+ cells compared to an unselected population.

The invention will be further understood with reference to the following illustrative embodiments, which are purely exemplary, and should not be taken as limiting the true scope of the present invention as described in the claims.

EXAMPLE 1

Syngeneic BMT (SBMT) in Mice Followed by Allo-CMI or Allo-CCI

I. METHODS

A. Mice

BALB/c (BALB), C57BL/6 (C57), and (BALB/c x C57BL/6)F1 (F1) mice, 2–6 months old, were purchased from the breeding colony of the Hebrew University-Hadassah Medical School, Jerusalem. Mice were kept under standard conditions, with acidic water (ph 2.7) and no special protective measures. Mice were given 0.5% neomycin sulfate in their drinking water for 2 weeks post-transplantation.

B. Murine B-Cell Leukemia (BCL1)

BLC1, a spontaneous, transplantable B-cell leukemia/lymphoma of BALB origin is characterized by marked (up to 50 fold) splenomegaly, accompanied by extreme peripheral blood lymphocytosis (>200,00/mm$^3$) and results in death of all mice inoculated with $\geq$10–100 tumor cells. Slavin et al., Nature 272:624 (1978); Slavin et al., Cancer Res. 41:4162 (1981). BCL1 was maintained in vivo in BALB mice by IV passage of $10^6$–$10^7$ peripheral blood lymphocytes (PBL) obtained from tumor bearing mice. Mice with marked lymphocytosis in the blood were subsequently used as BCL1 cell donors for experimental mice. PBL counts for all experimental groups were carried out weekly. Leukemia was defined as PBL counts exceeding 20,000/mm$^3$. At the peak of disease, PBL counts usually reached >100,000/mm$^3$.

C. Mafosfamide (ASTA-Z)

ASTA-Z was kindly provided by Drs M. Peukert and H. Sindermann (Astawerke, Bielefeld, Germany) as a lyophilized powder and was freshly dissolved in saline before use. ASTA-Z has been employed in vitro to reduce or eliminate malignant cell populations from bone marrow preparations. Douay et al., CR Acad.Sci.Paris t. 301, Ser III, no. 6:303 (1985).

D. Conditioning with Radiation and Cyclophosphamide Prior to BMT

Mice were exposed to a single dose of 750 cGy total body irradiation (TBI) from a Philips X-ray unit (250 kV 20 mA) with a focus to skin distance of 70 cm at a dose rate of 60 cGy/min. Alternatively, mice were conditioned with freshly dissolved cyclophosphamide (CY) (300 mg/kg) (Taro, Israel) given intraperitoneally (IP). Twenty-four hours later, mice received $10^7$ syngeneic marrow cells via the lateral tail vein.

E. Preparation of Bone Marrow Cells (BMC)

BMC were obtained from the femora, tibiae and humeri of syngeneic mice. Mononuclear cells containing $10^7$ BMC in 0.25 ml Hank's medium were injected into the lateral tail vein of recipients 24 hours post-radiation.

F. Purging Procedure

Cells were resuspended at a concentration of 20×10$^6$ cells/ml in Hank's medium containing 4% human serum albumin. ASTA-Z was then added to a final concentration of 100 μg/ml. Both untreated control cells and ASTA-Z treated BMC were incubated at 37° C. for 30 minutes, washed twice in Hank's medium and counted. Purged or unpurged BMC (4×10$^6$) were injected into BALB mice conditioned with CY.

G. Recombinant Human Interleukin-2 (rhIL2)

rhIL2 provided as 1 mg Proleukin (3×10$^6$ Cetus Units, equivalent to 18×10$^6$ International Units) was kindly supplied by Dr. S. L. Aukerman, Cetus/Chiron, Calif., USA. rhIL2 was initially diluted with water for injection and subsequently rediluted with dextrose 5%. International units (IU) are used throughout the remainder of the present application.

H. Activation of BMC by rhIL2

BMC were cultured in 225 cm$^3$ flasks (Corning 25160-225, Corning Glass, Corning N.Y.) in RPMI 1640 medium (Beit Haemek, Israel) containing L-glutamine, non-essential amino acids, pyruvate, 10% bovine calf serum (BCS) and rhIL2 (6,000 IU/ml) for 4 days in a humidified incubator with 5% $CO_2$ at 37° C. Following harvesting, viability was determined by the trypan blue exclusion method.

I. Simulation of Minimal Residual Disease Following Syngeneic Bone Marrow Transplantation In order to simulate minimal residual disease (MRD) quantitatively, 10$^5$ BCL1 cells were added to the marrow inoculum during syngeneic bone marrow transplantation (SBMT), prior to immunotherapy.

J. Immunotherapy by Immunocompetent Allogeneic Lymphocytes

Allogeneic cell-mediated immunotherapy (Allo-CMI) consisted of adoptive transfer of immunocompetent allogeneic lymphocytes (PBL or a mixture of donor spleen and lymph node cells) as detailed in the results for each experiment, below. Allogeneic cell-mediated cytokine-activated immunotherapy (Allo-CCI) consisted of adoptive transfer of allogeneic lymphocytes pre-activated in vitro with T-cell activator (activated donor lymphocytes, or "ADL"). In this EXAMPLE, T-cell activator comprised rhIL2. In some experiments allogeneic lymphocyte infusion was followed by subsequent in vivo activation with rhIL2, by additional Allo-CMI with in vivo rhIL-2, or by additional Allo-CCI with in vivo rhIL-2, respectively.

K. Detection of Residual Clonogenic BCL1 by Adoptive Transfer Experiments

In order to determine whether or not residual BCL1 cells were present after various treatments, 10$^5$ spleen cells obtained from treated mice were adoptively transferred to untreated secondary syngeneic (BALB) recipients. Absence of leukemia ($\geq$100 days) in secondary recipients was indicative of elimination of BCL1 since as few as 1–10 cells were previously shown to cause disease.

L. Statistical Analysis

The significance of differences between treated and untreated mice was calculated by the independent statistical t-test.

II. RESULTS

A. Induction of Allo-CMI and Allo-CCI Effects

F1 mice were lethally irradiated (750 cGy) and transplanted with 10$^7$ syngeneic BMC. Following inoculation of 10$^5$ BCL1 cells to simulate MRD, varying numbers of C57 PBL were administered intravenously to induce GVL-like effects through allo-CMI. In order to detect the efficacy of allo-CMI in eradicating residual BCL1 cells, aliquots of 10$^5$ spleen cells pooled from 2–3 experimental mice were adoptively transferred to secondary normal BALB recipients, one or two weeks post-SBMT.

FIG. 1 summarizes results obtained from three different experiments in a total of 120 mice. Injection of 20–30×10$^6$ PBL, obtained from C57 mice to induce allo-CMI after SBMT in F1 recipients, effectively eliminated residual BCL1 cells, as none of 40 secondary adoptive BALB recipients developed leukemia (>180 days). In contrast, leukemia developed in all 20 secondary BALB recipients inoculated with 10$^5$ spleen cells obtained from F1 recipients that had received 20–30×10$^6$ PBL from syngeneic donors post-SBMT. Addition of rhIL2 (12×10$^4$ IU×2/day for 5 days IP) post-transplant did not improve the disease-free survival of secondary recipients of $10^5$ spleen cells (obtained from similarly treated F1 mice) since all 20 secondary recipient BALB mice developed leukemia (FIG. 1). Addition of rhIL2 in vivo at the same dose to recipients of $20 \times 10^6$ allogeneic PBL for further in vivo activation of effector cells did not induce measurable additional GVL effects since all 40 secondary BALB recipients remained disease free (>180 days) (FIG. 1).

Figure 2:
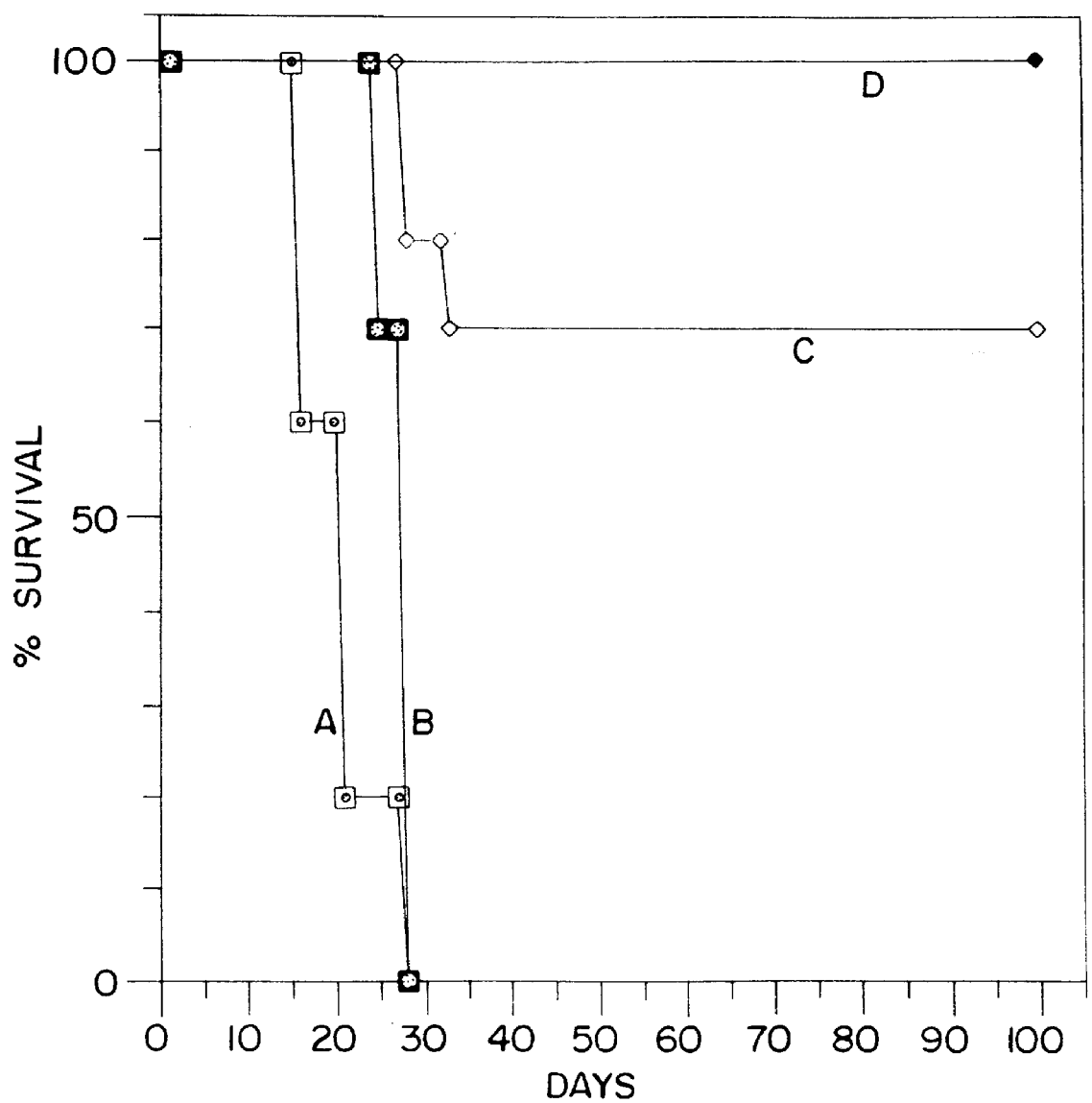
FIG. 2 depicts the results of adoptive transfer of spleen cells obtained from lethally irradiated F1 mice reconstituted with $10^7$ syngeneic bone marrow cells mixed with $10^5$ BCL1 cells. Cell-mediated immunotherapy consisted of intravenous administration of increasing numbers of C57BL/6 spleen cells: $1\times10^6$ (A, n=10); $3\times10^6$ (B, n=10); $10\times10^6$ (C, n=10) and $30\times10^6$ (D, n=10). One of three experiments is shown.

B. quantitative Effect of the Number of Effector Cells on the Efficacy of Allo-CMI Anti-leukemic effects mediated by allo-CMI were cell-dose dependent. As shown in FIG. 2, all SBMT recipients injected with $30 \times^6$ C57 spleen cells completely resisted the development of leukemia following inoculation of $10^5$ BCL1 cells. Injection of $10 \times 10^6$ allogeneic spleen cells together with $10^5$ BCL1 cells induced effective allo-CMI in 70% of the secondary adoptive recipients. However, reduction of allo-CMI inducing C57 spleen cells to $3 \times^6$ or $1 \times^6$ failed to eliminate residual BCL1 cells and all secondary adoptive recipients developed leukemia (FIG. 2).

C. Induction of Allo-CMI and Allo-CMI/Il-2 Effects Following Transplantation with ASTA-Z-Purged BMC The feasibility of induction of allo-CMI was investigated by conditioning with high-dose CY followed by rescue of recipients with ASTA-Z-purged syngeneic BMC. BALB recipients received high-dose CY (300 mg/kg IP) and were injected 24 hours later with $10^3$ BCL1 cells to simulate MRD. One day later, all mice received intravenously $4 \times^6$ ASTA-Z treated syngeneic BMC. Mice were divided into 3 experimental groups: the first group (6 mice) received intravenously a mixture of allogeneic C57 spleen and lymph node cells ($20 \times^6$ cells) for induction of allo-CMI; the second group (6 mice) received identical cell therapy with additional in vivo potentiation of GVL by rhIL2 treatment ($12 \times^4$ IU$\times$3/day for 3 days, IP); the third group (7 mice) received a mixture of syngeneic spleen and lymph node cells, with an identical in vivo rhIL2 treatment. One week later, aliquots of $10^5$ cells from a pool of 2–3 spleens obtained from each experimental group were adoptively transferred to secondary BALB mice.

Figure 3:
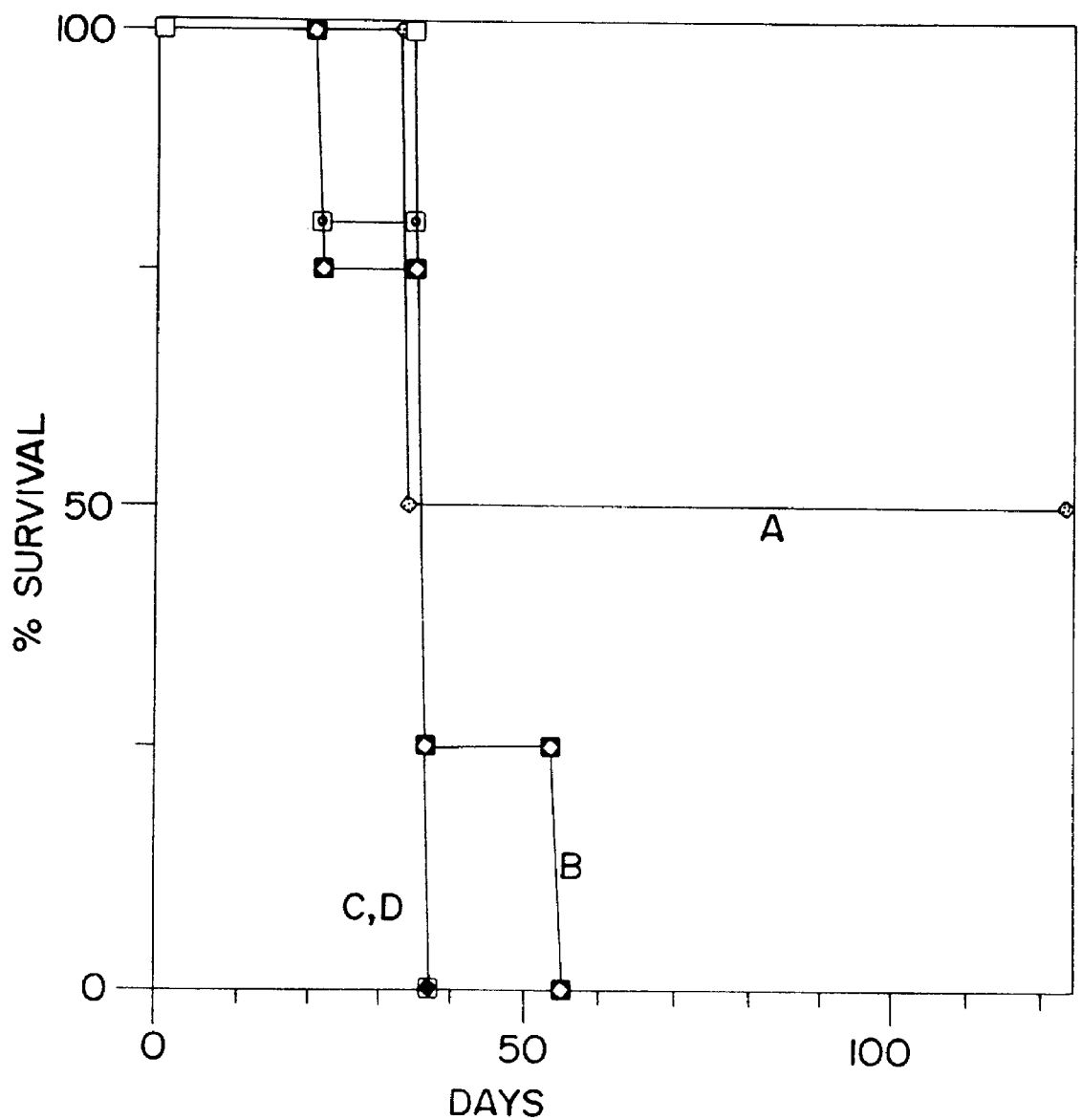
FIG. 3 depicts results of adoptive transfer of spleen cells obtained from BALB/c mice treated with cyclophosphamide (300 mg/kg IP), inoculated 24 hours later with $10^3$ BCL1 cells, and one day later receiving $4\times10^6$ syngeneic, ASTAZ-treated bone marrow cells. Immunotherapy consisted of a mixture of $20\times10^6$ allogeneic C57BL/6 spleen and lymph node cells either with (A, n=6) or without (B, n=6) rhIL2 treatment in vivo ($12\times10^4$ IU×3/day for 3 days IP). Recipients of a mixture of $20\times10^6$ syngeneic BALB/c spleen and lymph node cells treated with rhIL2 (C, n=7) and recipients of $10^3$ BCL1 cells only (D, n=10) served as controls.

As shown in FIG. 3, all mice inoculated with spleen cells from control mice given $10^3$ BCL1 cells, or mice given syngeneic BALB lymphocytes with in vivo rhIL2, developed leukemia and died within 40 and 60 days, respectively. Likewise, secondary recipients of $10^5$ spleen cells obtained from mice that were treated with allo-CMI, using allogeneic C57 cells alone, showed no measurable GVL effects since all recipients developed leukemia. In contrast, addition of rhIL2 in vivo following administration of C57 spleen and lymph node cell mixtures induced substantial anti-leukemic effects and 50% of the secondary adoptive recipient mice remained leukemia-free for >125 days (FIG. 3).

D. Enhancement of Immunotherapeutic Effect by In Vitro Activation of Allogeneic Lymphocytes with rhIL2

Figure 4:
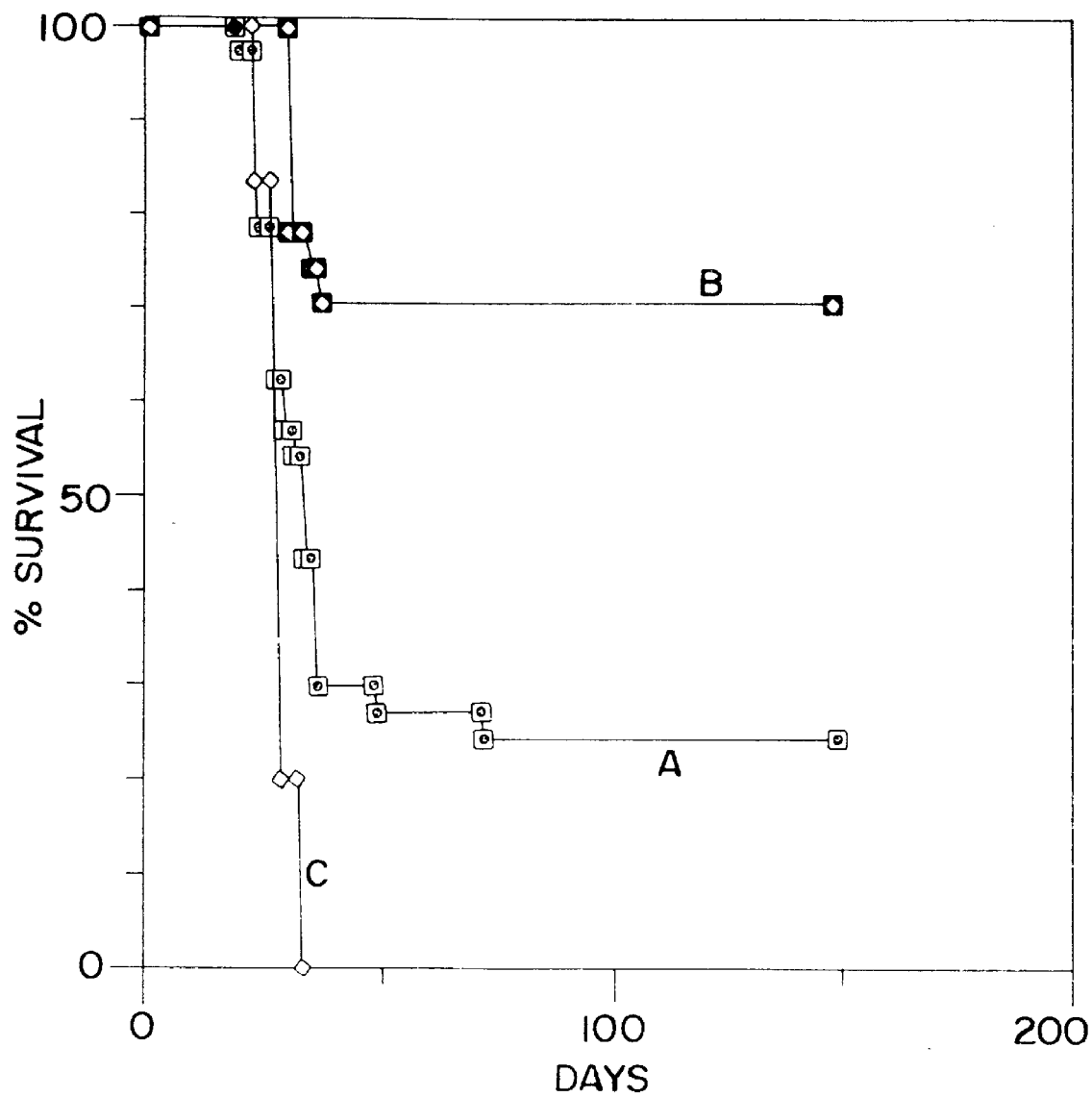
FIG. 4 depicts the results of adoptive transfer of spleen cells obtained from lethally irradiated F1 mice inoculated with $10^5$ BCL1 cells and $30 \times 10^6$ bone marrow cells pre-activated in vitro for 4 days with rhIL2; mice with no additional treatment (A, n=33), mice with in vivo rhIL2 treatment ($12 \times 10^4$ IU$\times$2/day for 5 days IP) (B, n=25); controls: recipients of $10^5$ spleen cells obtained from untreated control mice inoculated with $10^5$ BCL1 cells (C, n=30).

The following experiment was designed to test for potential enhancements in efficacy of treatment by in vitro pre-activation of allogeneic effector cells with rhIL2. Lethally irradiated (750 cGy TBI) F1 mice were infused with $30 \times^6$ C57 BMC pre-activated in vitro for 4 days with rhIL2. BMC were mixed with $10^5$ BCL1 cells to simulate MRD. Results of 3 separate sets of experiments gave similar results and therefore the data were pooled (FIG. 4).

All F1 recipients were divided into two groups. The first group of 33 mice received no additional treatment. Mice in the second group (25 mice) were injected with rhIL2 ($12 \times^4$ IU$\times$2/day for 5 days, IP) in an attempt to further increase efficacy of cell therapy by continuous activation of rhIL2-dependent effector cells in vivo. Aliquots of $10^5$ cells obtained from a pool of spleen cells prepared from mice of either experimental group were adoptively transferred to secondary BALB recipients. As shown in FIG. 4, 10 of 33 secondary recipients of spleen cells obtained from the first experimental group remained disease-free for >150 days. Additional in vivo rhIL2 therapy in the second experimental group further improved the Allo-CCI effects, as 19 of 25 secondary recipients remained disease-free for an observation period >150 days (p=0.05) (FIG. 4).

EXAMPLE 2

Autologous Stem Cell Transplantation (ASCT) in Humans Followed by Allo-CMI and/or Allo-CCI

I. PATIENT TREATMENT PROTOCOLS

Patient No. 1

This female patient was diagnosed with acute myelogenous leukemia (AML), French American British (FAB) classification M4, and was in first complete remission (i.e., no evidence of disease) at the time of autologous stem cell transplantation (ASCT). The patient was 41 years old at the time of ASCT. Prior to ASCT, she received a conditioning regimen of Busulfan, 4 mg/kg, days 6 through 9 pre-ASCT (days −9 to −6), as well as Cytoxan (cyclophosphamide), 50 mg/kg, days −5 to −2, Cotrimoxazol, 10 mg/kg, days −10 to −2, Allopurinol, 300 mg/kg, days −10 to −1 and cytosine arabinoside (Ara-C), 25 mg intrathecally.

Prior to ASCT, the autologous cells to be infused were purged by treatment with Mafosfamide (ASTA-Z). ASTA-Z was provided by Drs. M. Peukert and H. Sindermann (Astawerke, Bielefeld, Germany) as a lyophilized powder and was freshly dissolved in saline before use. Autologous cells were resuspended at a concentration of $20 \times 10^6$ cells/ml in Hank's medium containing 4% human serum albumin. ASTA-Z was then added to a final concentration of 100 ug/ml and the cells were incubated in the ASTA-Z at 37° C. for 30 min. After this, the cells were washed twice in Hank's medium and counted. Cells were cryopreserved and kept in liquid nitrogen until used. ASCT consisted of $2.5 \times 10^8$ nucleated bone marrow cells/kg, infused intravenously (IV) on day 0.

On day 1 following ASCT (day +1), the patient received $10^4$ T cells/kg of peripheral blood lymphocytes (PBL) from an HLA-matched donor. On days +8, +22, +29 and +36 she received PBL from the same donor at an equivalent dose of $10^5$, $10^5$, $10^6$, and $10^6$ T cells/kg, respectively. On day +47 she received PBL from the same donor at an equivalent dose of $10^7$ T cells/kg. The patient showed no evidence of GVHD.

Patient No. 2

This female patient was diagnosed with AML, FAB M5, and was in first complete remission at the time of ASCT. The patient was 42 years old at the time of ASCT. Prior to ASCT, she received a conditioning regimen of Busulfan, 4 mg/kg, (days −9 to −6), as well as Cytoxan, 50 mg/kg, days −5 to −2, Cotrimoxazol, 10 mg/kg, days −10 to −2, Allopurinol, 300 mg/kg, days −10 to −1 and Ara-C, 25 mg intrathecally.

Prior to ASCT, the autologous bone marrow cells to be infused were purged by treatment with ASTA-Z. Autologous cells were resuspended at a concentration of $20 \times 10^6$ cells/ml in Hank's medium containing 4% human serum albumin. ASTA-Z was then added to a final concentration of 100 ug/ml and the cells were incubated in the ASTA-Z at 37° C. for 30 min. After this, the cells were washed twice in Hank's medium, counted and cryopreserved. ASCT consisted of $1 \times 10^8$ nucleated bone marrow cells/kg, infused IV on day 0.

One day +1, the patient received $10^4$ T cells/kg to PBL from an HLA-matched donor. On days +8, +18 and +26 she received PBL from the same donor at an equivalent dose of $10^5$, $10^6$, and $10^7$ T cells/kg, respectively. One day +80 she received PBL from the same donor at an equivalent dose of $10^7$ T cells/kg, with $3\times10^6$ IU of rhIL-2/m$^2$/day for 3 days, by subcutaneous injection beginning on day +80. The patient showed no evidence of GVHD.

Patient No. 3

This female patient was diagnosed with AML, FAB M3, and was in first complete remission at the time of ASCT. The patient was 32 years old at the time of ASCT. Prior to ASCT, she received a conditioning regimen of Busulfan, 4 mg/kg, (days −9 to −6), as well as Cytoxan, 50 mg/kg, days −5 to −2, Cotrimoxazol, 10 mg/kg, days −10 to −2, Allopurinol, 300 mg/kg, days −10 to −1, and Ara-C, 25 mg intrathecally. ASCT consisted of non-purged bone marrow cells, and $0.79\times10^8$ nucleated cells/kg were infused IV on day 0. On day +1, the patient received PBL from an HLA-matched donor at an equivalent dose of $10^7$ T cells/kg. On day +1, she also received $6\times10^6$ IU of rhIL-2/m$^2$ by subcutaneous injection. No GVHD was observed.

Patient No. 4

This male patient was diagnosed with AML, FAB M2, and was in first complete remission at the time of ASCT. The patient was 23 years old at the time of ASCT. Prior to ASCT, he received a conditioning regimen of Busulfan 4 mg/kg, days −9 to −6, Cytoxan 60 mg/kg, days −3 to −2, Thiotepa 5 mg/kg/day, days −5 to −4, Cotrimoxazol, 10 mg/kg, days −10 to −2, Allopurinol, 300 mg/kg, days −10 to −1 and Ara-C, 25 mg intrathecally. ASCT consisted of non-purged $1.37\times10^8$ nucleated bone marrow cells/kg, infused IV on day 0. On day +1, the patient received PBL from an HLA-matched donor at an equivalent dose of $10^7$ T cells/kg. On day +1, he also received $6\times10^6$ IU of rhIL-2/m$^2$ by subcutaneous injection. GVHD was suspected (Grade I) in the skin.

Patient No. 5

This male patient was diagnosed with chronic myelogenous leukemia (CML) in chronic phase. The original CML karyotype was positive for the Philadelphia chromosome (Ph+). The patient was in chronic phase (CP) and was Ph− at the time of ASCT. The patient was 57 years old at the time of ASCT. Prior to ASCT, he received a conditioning regimen of total body irradiation (TBI) 200 cGy/day, days −5 to −3, and Cytoxan 60 mg/kg, days −2 to −1. ASCT consisted of non-purged $0.5\times10^8$ nucleated bone marrow cells/kg, infused IV on day 0.

On day +71, as soon as blood counts had stabilized (WBC: 4,200/mm$^3$; Hb: 11.5 gt; platelets: 133,000/mm$^3$), the patient received $3\times10^7$ T cells/kg of PBL from an HLA-/matched brother. No GVHD was observed; hence; the allo-CMI regimen was escalated. On day +$10^7$, the patient received $4.6\times10^7$ T cells/kg of PBL from the same donor. Starting on day +$10^7$, he also received $6\times10^6$ IU of rhIL2/m$^2$/day for 3 days, by subcutaneous injection. No GVHD was observed. On day +240, after the Ph+ karyotype had reappeared, the patient received $4.95\times10^7$ cell/kg of activated donor lymphocytes ("ADL") from the same donor. Starting on day +240, he also received $6\times10^6$ IU of rhIL-2/m$^2$/day for 3 days, by subcutaneous injection. The ADL were produced by exposing the donor's PBL to 6,000 IU/ml rhIL2 for four days in culture.

Patient No. 6

This female patient was diagnosed with AML, FAB M2, and was in first complete remission at the time of ASCT. The patient was 50 years old at the time of ASCT. Prior to ASCT, she received a conditioning regimen of Busulfan 4 mg/kg, days −9 to −6, Cytoxan 60 mg/kg, days −3 to −2, Thiotepa 5 mg/kg/day, days −5 to −4, Cotrimoxazol, 10 mg/kg, days −10 to −2, Allopurinol, 300 mg/kg/days −10 to −1 and Ara-C, 25 mg intrathecally. ASCT consisted of non-purged $0.64\times10^8$ nucleated bone marrow cells/kg infused IV on day 0. On day +58, as soon as blood counts had stabilized (WBC:4,400/mm$^3$; Hb:9.5 g %; platelets:66,000/mm$^3$), the patient received $5\times10^7$ T cells/kg of PBL from an HLA-matched sister. On day +86 the patient received a second dose of $6.1\times10^7$ cells/kg of PBL from the HLA-matched sister. Starting on day +86, she also received $6\times10^6$ IU of rhIL-2/m$^2$/day for 3 days, by subcutaneous injection. No GVHD was observed.

Patient No. 7

This male patient was diagnosed with CML. The original CML karyotype was Ph+. The patient was in chronic phase (CP) and 50% of his marrow cells were Ph+ (i.e., the patient was Ph+) at the time of ASCT. The patient was 47 years old at the time of ASCT. Prior to ASCT, he received a conditioning regimen of TBI 200 cGY/day, days −5 to −3, and Cytoxan 60mg/kg, days −2 to −1. ASCT consisted of non-purged $0.98\times10^8$ nucleated bone marrow cells/kg, infused IV on day 0. On day +55, as soon as blood counts had stabilized (WBC:6,900/mm$^3$;Hb:12.0 g %;platelets:248,000/mm$^3$), the patient received $4\times10^7$ T cells/kg of PBL from an HLA-matched sister. No GVHD developed. On day +77, the patient received $2.8\times10^7$ cells/kg of PBL from the HLA-matched sister. Starting on day +77, he also received $6\times10^6$ IU of rhIL-2/m$^2$/day for 3 days, by subcutaneous injection. No GVHD was observed.

Patient No. 8

This male patient was diagnosed with non-Hodgkin's lymphoma (NHL), Burkitt-like, and was in a second partial remission at the time of ASCT. As used herein, the term "partial remission" indicates at least a 50% response (i.e., at least a 50% reduction of lymphoma cells mass) but with continued evidence of disease. The patient was 36 years old at the time of ASCT. Prior to ASCT, he received a conditioning regimen of etoposide, 200 mg/m$^2$/day, days −6 to −3, thiotepa, 40 mg/m$^2$/day, days −5 to −2, Ara-C, 200 mg/m$^2$/day, days −4 to −1, Cytoxan, 60mg/kg/day, day −3, and melphalan, 60 mg/m$^2$/day, days −2 to −1.

ASCT consisted of $0.74\times10^8$/kg viable bone marrow nucleated cells plus $2.36\times10^8$/kg viable peripheral blood stem cells. Subcutaneous GM-CSF, 5 ug/kg/day, was administered from day +1 to day +18. Prior to ASCT, the autologous cells were purged with Dynal magnetic beads coated with anti-CD19 for elimination of residual lymphoma cells.

On day +90, the patient received $5\times10^7$ cells/kg of PBL from an HLA-matched brother. The patient showed no signs of GVHD following this first cell infusion. Polymerase chain reaction (PCR) analysis using two VNTR loci (VNTR =Variable Number of Tandem Repeats) revealed no evidence of circulating donor-specific cells. On day +124, the patient received $5\times10^7$ cells/kg of PBL from the same donor. This was followed by three days of outpatient treatment with $6\times10^6$ IU of rhIL-2/m$^2$/day, by subcutaneous injection, beginning on day +124.

Fifty days later (day +174) the patient developed pancytopenia, and bone marrow biopsy revealed severe hypocellular marrow with increased numbers of large granular lymphocytes and plasma cells. Lymphocytes with a similar morphology were found in the blood. Repeated PCR using two different VNTR loci showed partial engraftment of donor cells on day +191 and 100% engraftment of donor cells on day +211. An allogeneic BMT was then performed by infusing the patient with $4.2 \times 10^8$/kg of the donor's marrow cells; no post-transplant anti-GVHD prophylaxis was administered. The patient had rapid three-lineage engraftment with normal platelet counts after 14 days and normal hemoglobin after 26 days. WBC normalized after 10 days with 70% neutrophil, 5% monocytes and 25% lymphocytes. Large granular lymphocytes disappeared from the blood. On day 14 following allogeneic BMT, the patient showed minimal signs of acute GVHD with involvement of skin and oral cavity. There was no intestinal or liver involvement. Since then the patient has continue to experience grade I/II mucocutaneous GVHD, partially controlled with steroids and cyclosporin A.

Patient No. 9

This male patient was diagnosed with NHL, follicular mixed IV A, and was in a second partial remission at the time of ASCT. The patient was 39 years old at the time of ASCT. Prior to ASCT, he received a conditioning regimen of etoposide, 200 mg/m$^2$/day, days –6 to –3; thiotepa, 40 mg/m$^2$/day, days –5 to –2; Ara-C, 200 mg/m$^2$/day, days –4 to –1; Cytoxan, 60 mg/kg/day, day –3; and melphalan, 60 mg/m$^2$/day, days –2 to –1.

ASCT consisted of $0.5 \times 10^8$ nucleated bone marrow cells/kg, infused IV on day 0. Prior to ASCT, the autologous cells were purged with Dynal magnetic beads coated with anti-CD19 for elimination of contaminating tumor cells.

At week 8 post-ASCT, the patient received $5 \times 10^7$ T cells/kg of PBL from an HLA-matched sister. At week 12 post-ASCT, the patient received $5 \times 10^7$ T cells/kg of PBL from the same donor. Starting at week 12, on the same day as the administration of the second Allo-CMI treatment, the patient also received $6 \times 10^6$ IU of rhIL-2/m$^2$/day for 3 days, by subcutaneous injection. No GVHD was observed. At week 16 post-ASCT, the patient received $0.5 \times 10^7$ ADL/kg from the HLA-matched sister. The ADL were produced by exposing the donor's PBL to 6,000 IU/ml rhIL-2 for four days in culture. No GVHD was observed.

Patient No. 10

This female patient was diagnosed with NHL, mixed cellularity II A, and was in a second complete remission at the time of ASCT. The patient was 36 year old at the time of ASCT. Prior to ASCT, she received a conditioning regimen of etoposide, 200 mg/m$^2$/day, days –6 to –3, thiotepa, 40 mg/m$^2$/day, days –5 to –2, Ara-C, 200 mg/m$^2$/day, days –4 to –1, Cytoxan, 60 mg/kg/day, day –3, and melphalan, 60 mg/m$^2$/day, days –2 to –1.

ASCT consisted of $0.94 \times 10^8$ non-purged nucleated bone marrow cells/kg plus $3.9 \times 10^7$ peripheral blood stem cells mobilized by G-CSF prior to collection with the CS 3000® Plus blood cell separator (Baxter Healthcare Corporation, Fenwal System Catalogue No. 4R4538). Cells were infused IV on day 0.

At week 10 post-ASCT, as soon as blood counts had stabilized (WBC:4,300/mm$^3$; Hb: 11.2 g %; platelets: 116,000/mm$^3$), the patient received $3 \times 10^7$ T cells/kg of PBL from an HLA-matched brother. At week 15 post-ASCT, the patient received $4.1 \times 10^7$ T cells/kg of PBL from the same donor. Starting at week 15, on the same day as the administration of the second Allo-CMI treatment, the patient also received $6 \times 10^6$ IU of rhIL-2/m$^2$/day for 3 days, by subcutaneous injection. At week 23 post-ASCT, the patient received $5 \times 10^7$ ADL/kg from the HLA-matched brother. The ADL were produced by exposing the donor's PBL to 6,000 IU/ml rhIL-2 for four days in culture. Starting at week 23, on the same day as the administration of the Allo-CCI treatment, the patient also received $6 \times 10^6$ IU of rhIL-2/m$^2$/day for 3 days, by subcutaneous injection. No GVHD was observed.

Patient No. 11

This female patient was diagnosed with NHL, immunoblastic, and was in a second complete remission at the time of ASCT. The patient was 21 years old at the time of ASCT. Prior to ASCT, she received a conditioning regimen of etoposide, 200 mg/m$^2$/day, days –6 to –3; thiotepa, 40 mg/m$^2$/day, days –5 to –2; Ara-C, 200 mg/m$^2$/day, days –4 to –1; Cytoxan, 60 mg/kg/day, day –3; and melphalan, 60 mg/m$^2$/day, days –2 to –1.

ASCT consisted of $3.82 \times 10^8$ non-purged bone marrow cells/kg plus $1.29 \times 10^8$ peripheral blood stem cells mobilized with G-CSF prior to collection with the CS 3000® Plus blood cell separator. Cells were infused IV on day 0.

At week 10 post-ASCT, the patient received $5 \times 10^7$ T cells/kg of PBL from an HLA-matched sister. At week 15 post-ASCT, the patient received a second infusion of $5 \times 10^7$ T cell/kg of PBL from the HLA-matched sister. At week 19 post-ASCT, the patient received a third infusion of $5 \times 10^7$ T cells/kg of PBL from the same donor. No GVHD was observed, but the patient did not accept the suggestion that she receive in vivo rhIL2. At week 30 post-ASCT, the patient received a fourth infusion of $5 \times 10^7$ T cells/kg of PBL from the HLA-matched sister. Starting at week 23, on the same day as the administration of the fourth Allo-CMI treatment, the patient also received $6 \times 10^6$ IU of rhIL-2/m$^2$/day for 3 days, by subcutaneous injection. No GVHD has been observed to date.

Patient No. 12

This female patient was diagnosed with NHL, diffuse large cell, and was in condition of relapse at the time of ASCT. The patient was 21 years old at the time of ASCT. Prior to ASCT, she received a conditioning regimen of etoposide, 200 mg/m$^2$/day, days –6 to –3; thiotepa, 40 mg/m$^2$/day, days –5 to –2; Ara-C, 200 mg/m$^2$/day, days –4 to –1; Cytoxan, 60 mg/kg/day, day –3; and melphalan, 60 mg/m$^2$/day, days –2 to –1.

ASCT consisted of $1.8 \times 10^8$ non-purged mononuclear bone marrow cells/kg, infused IV on day 0.

At week 6 post-ASCT, as soon as blood counts had stabilized (WBC: 4,400/mm$^3$; Hb:11.7 g %; platelets: 150,000/mm$^3$), the patient received $5 \times 10^7$ T cells/kg of PBL from a single locus-mismatched sister. At week 10 post-ASCT, the patient received a second infusion of $5 \times 10^7$ T cell/kg of PBL from the same donor. Starting at week 10, on the same day as the administration of the second Allo-CMI treatment, the patient also received $6 \times 10^6$ IU of rhIL-2/m$^2$/day for 3 days, by subcutaneous injection. No GVHD was observed.

Patient No. 13

This male patient was diagnosed with AML, FAB M5, and was in first complete remission at the time of ASCT. The patient was 46 years old at the time of ASCT. Prior to ASCT, he received a conditioning regimen of Busulfan 4/ mg/kg, days –9 to –6; Cytoxan 60 mg/kg, days –3 to –2; Thiotepa, 5 mg/kg/day, days –5 to –4; Cotrimoxazol, 10 kg/mg, days –10 to –2, Allopurinol, 300 mg/kg, days –10 to –1 and Ara-C, 25 mg intrathecally. ASCT consisted of $1.39 \times 10^8$ non-purged bone marrow cells infused IV on day 0. At week 11, the patient received $3.86 \times 10^7$ T cells/kg of PBL from an HLA-matched brother. No GVHD developed.

Patient No. 14

This female patient was diagnosed with AML, FAB M3, and was in second partial remission at the time of ASCT. The patient was 12 years old at the time of ASCT. Prior to ASCT, she received a conditioning regimen of Busulfan 4 mg/kg, days –9 to –6; Cytoxan 60 mgkg, days –3 to –2; Mitoxantrone 6 mg/m$^2$/day, days –5 to –4; Cotrimoxazol, 10 mg/kg, days −10 to −2, Allopurinol, 300 mg/kg, days −10 to −1 and Ara-C, 25 mg intrathecally. ASCT consisted of $1.14\times10^8$ non-purged marrow cells infused IV on day 0. On day +113, the patient received $2\times10^7$ T cells/kg of single locus-mismatched PBL from her mother. On day +142, the patient received 1000 mg/m² Cytoxan in order to improve the efficacy and temporal engraftment of a second infusion of the donor's PBL. Twenty four hours later, the patient received $1.7\times10^7$ T cells/kg from the same donor. Starting on the same day as the administration of the second Allo-CMI treatment, the patient also received $6\times10^6$ IU of rhIL-2/m²/day for 3 days, by subcutaneous injection. On day +188, the patient received $1.5\times10^7$ ADL/kg from the same donor. The ADL were produced by exposing the donor's PBL to 6,000 IU/ml rhIL-2 for four days in culture. On the same day as the administration of the Allo-CCI treatment, the patient also received $6\times10^6$ IU of rhIL-2/m²/day for 3 days, by subcutaneous injection.

Patient No. 15

This male patient was diagnosed with AML, FAB M5, and was in first complete remission at the time of ASCT. The patient was 6 ½ years old at the time of ASCT. Prior to ASCT, he received a conditioning regimen of Busulfan 4 mg/kg, days −9 to −6; Cytoxan 60 mg/kg, days −3 to −2; Thiotepa 5 mg/kg/day, days −5 to −4; Cotrimoxazol, 10 mg/kg, days −10 to −2, Allopurinol, 300 mg/kg, days −10 to −1 and Ara-C, 25 mg intrathecally. ASCT consisted of $2.7\times10^8$ non-purged marrow cells infused IV on day 0. At week 14, the patient received $5\times10^7$ T cells/kg of single locus-mismatched PBL from his father. The patient later (May 3, 1994) received $2.5\times10^7$ T cells/kg of single locus-mismatched PBL from the same donor. On the same day as the administration of the second Allo-CMI treatment, the patient also received $6\times10^6$ IU of rhIL-2/m²/day for 3 days, by subcutaneous injection. Prior to the second Allo-CMI treatment, the patient received cytoxan at 500–1,000 mg/m² with adequate hydration. One month later the patient received $7.8\times10^7$ ADL/kg from the same donor. The ADL were produced by exposing the donor's PBL to 6,000 IU/ml rhIL-2 for four days in culture. Beginning on the same day as the administration of the Allo-CCI treatment, the patient also received $6\times10^6$ IU of rhIL-2/m²/day for 3 days, by subcutaneous injection. Prior to the Allo-CCI treatment, the patient received cytoxan at 500–1,000 mg/m² with adequate hydration.

Patient No. 16

This male patient was diagnosed with NHL, mixed large and small cell, in the lymph nodes, in February of 1993. There was also heavy bone marrow involvement. He received chemotherapy (12 courses of MACOP-B), but relapsed in the lymph nodes and bone marrow in October of 1993. He underwent additional chemotherapy and was in a second partial remission at the time of ASCT, with recurrence in the marrow. The patient was 45 years old at the time of ASCT. Prior to ASCT, he received a conditioning regimen consisting of etoposide, 200 mg/m²/day, days −6 to −3; thiotepa, 40 mg/m²/day, days −5 to −2; Ara-C, 200 mg/m²/day, days −4 to −1; Cytoxan, 60 mg/kg/day, day −3; and melphalan, 60 mg/m²/day, days −2 to −1.

ASCT consisted of $2.15\times10^8$ non-purged G-CSF-mobilized peripheral blood stem cells, infused IV on day 0.

At week 7 post-ASCT, the patient received $3\times10^7$ T cells/kg of PBL from an HLA-matched sister. At week 11 post-ASCT, the patient received a second infusion of $3\times10^7$ T cell/kg of PBL from the same donor. Starting at week 11, on the same day as the administration of the second Allo-CMI treatment, the patient also received $6\times10^6$ IU of rhIL-2/m²/day for 3 days, by subcutaneous injection. Prior to the second Allo-CMI treatment, the patient received cyclophosphamide (cytoxan) at 500–1,000 mg/m² with adequate hydration. No GVHD was observed. To escalate the treatment, the patient received $3\times10^7$ ADL/kg from the HLA-matched donor. The ADL were produced by exposing the donor's PBL to 6,000 IU/ml rhIL-2 for four days in culture. On the same day as the administration of the Allo-CCI treatment, the patient also received $6\times10^6$ IU of rhIL-2/m²/day for 3 days, by subcutaneous injection. Prior to the Allo-CCI treatment, the patient received melphalan at 30 mg/m².

Notes on Patient No.'s 17–23

Patients 17–23 represent additional lymphoma patients treated similarly to patients 8–12 and 16, except that the initial infusion of allogeneic lymphocytes was accompanied by in vivo administration of rhIL2. Relevant aspects of the treatment protocols are summarized below:

Patient No. 17

This male patient was diagnosed with Hodgkins Disease, with nodular sclerosis, and was in a third partial remission at the time of ASCT. He was 16 years old at the time of ASCT. Prior to ASCT, he received a conditioning regimen as set out above for patient No. 16. The ASCT consisted of bone marrow cells only. Following partial hematopoietic recovery, the patient received $3\times10^7$ T cells/kg of PBL from an HLA-compatible sibling. On the same day as the administration of the first Allo-CMI treatment, the patient also received $6\times10^6$ IU of rhIL-2/m²/day for 3 days, by subcutaneous injection. Prior to the Allo-CMI treatment, the patient received cytoxan at 500–1,000 mg/m² with adequate hydration. No GVHD was observed. To escalate the treatment, the patient received $2.0\times10^7$ ADL/kg from the HLA-matched donor. The ADL were produced by exposing the donor's PBL to 6,000 IU/ml rhIL-2 for four days in culture. On the same day as the administration of the Allo-CCI treatment, the patient also received $6\times10^6$ IU of rhIL-2/m²/day for 3 days, by subcutaneous injection. Prior to the Allo-CCI treatment, the patient received cytoxan at 500–1,000 mg/m² with adequate hydration.

Patient No. 18

This female patient was diagnosed with NHL, Low Grade, and was in second complete remission at the time of ASCT. She was 24 years old at the time of ASCT. Prior to ASCT, she received a conditioning regimen as set out above for patient No. 16. The ASCT consisted of bone marrow cells ($1.95\times10^8$/kg) plus peripheral blood stem cells ($3.88\times10^8$/kg). On day +169, the patient received $3.6\times10^7$ T cells/kg of PBL from an HLA-compatible sister. On the same day as the administration of the first Allo-CMI treatment, the patient also received $6\times10^6$ IU of rhIL-2/m²/day for 3 days, by subcutaneous injection. Prior to the Allo-CMI treatment, the patient received cytoxan at 750 mg/m² with adequate hydration. No GVHD was observed. To escalate the treatment, the patient received (day +171) $3.0\times10^7$ ADL/kg from the HLA-matched donor. The ADL were produced by exposing the donor's PBL to 6,000 IU/ml rhIL-2 for four days in culture. On the same day as the administration of the Allo-CCI treatment, the patient also received $6\times10^6$ IU of rhIL-2/m²/day for 3 days, by subcutaneous injection. Prior to the Allo-CCI treatment, the patient received melphalan at 30 mg/m².

Twelve (12) days after administration of the ADL, the patient developed severe bone marrow aplasia. An allogeneic bone marrow transplant was performed with the matched PBL donor's bone marrow cells ($2.9\times10^8$/kg), depleted of immunocompetent T cells using the Campath- 1G, a monoclonal rat anti-human CDW52 (IgG2b) antibody, provided by Drs. G. Hale and H. Waldmann (Oxford University, UK). See, e.g., Hale et al., Campath-1 monoclonal antibodies in bone marrow transplantation. J. Hematotherapy 3: 15–31 (1994). The Campath-1G antibody was used at a concentration of 0.3 $\mu$g/$10^6$ nucleated cells. Granulocyte reconstitution was enhanced by daily subcutaneous administration of G-CSF (5 ug/kg/day). Subsequent to the allogeneic BMT, the patient totally recovered with normal 3-lineage engraftment of 100% donor-type hematopoietic cells and no residual host DNA, as attested to by VNTR-PCR. There was no acute GVHD, and no anti-GVHD prophylaxis was used.

Patient No. 19

This female patient was diagnosed with NHL, High Grade, with refractory disease. She was 48 years old at the time of ASCT. Prior to ASCT, she received a conditioning regimen as set out above for patient No. 16. The ASCT consisted of bone marrow cells and peripheral blood stem cells combined. Following partial hematopoietic recovery, the patient received $5.8\times10^7$ T cells/kg of PBL from an HLA-compatible sibling. On the same day as the administration of the first Allo-CMI treatment, the patient also received $6\times10^6$ IU of rhIL-2/$m^2$/day for 3 days, by subcutaneous injection. No GVHD was observed. To escalate the treatment, the patient received $3.8\times10^7$ ADL/kg from the HLA-matched donor. The ADL were produced by exposing the donor's PBL to 6,000 IU/ml rhIL-2 for four days in culture. On the same day as the administration of the Allo-CCI treatment, the patient also received $6\times10^6$ IU of rhIL-2/$m^2$/day for 3 days, by subcutaneous injection. Prior to the Allo-CCI treatment, the patient received melphalan at 30 mg/$m^2$.

Patient No. 20

This male patient was diagnosed with Hodgkins Disease, with nodular sclerosis, and was in a second complete remission at the time of ASCT. He was 49 years old at the time of ASCT. Prior to ASCT, he received a conditioning regimen as set out above for patient No. 16. The ASCT consisted of bone marrow cells only ($0.9\times10^8$/kg). On day +183, the patient received $8.3\times10^6$ T cells/kg of PBL from an HLA-compatible sister. On the same day as the administration of the Allo-CMI treatment, the patient also received $6\times10^6$ IU of rhIL-2/$m^2$/day for 3 days, by subcutaneous injection. Prior to the Allo-CMI treatment, the patient received cytoxan at 1,500 mg/$m^2$ with adequate hydration.

Twenty one (21) days following the Allo-CMI treatment, the patient developed bone marrow aplasia. An allogeneic bone marrow transplant was performed with the matched PBL donor's bone marrow cells ($3.3\times10^8$/kg), depleted of immunocompetent T cells using Campath-1G (0.3 $\mu$g/$10^6$ nucleated cells).

Patient No. 21

This female patient was diagnosed with NHL, High Grade, and was in second partial remission at the time of ASCT. She was 39 years old at the time of ASCT. Prior to ASCT, she received a conditioning regimen as set out above for patient No. 16. The ASCT consisted of bone marrow cells and peripheral blood stem cells combined. Prior to ASCT, the autologous cells were purged with Dynal magnetic beads coated with anti-CD19 for elimination of contaminating tumor cells. Following partial hematopoietic recovery, the patient received $2.7\times10^7$ T cells/kg of PBL from an HLA-compatible sibling. On the same day as the administration of the first Allo-CMI treatment, the patient also received $6\times10^6$ IU of rhIL-2/$m^2$/day for 3 days, by subcutaneous injection. Prior to the Allo-CMI treatment, the patient received cytoxan at 500–1,000 mg/$m^2$ with adequate hydration.

Patient No. 22

This male patient was diagnosed with Hodgkins Disease, with nodular sclerosis, and was in a third complete remission at the time of ASCT. He was 29 years old at the time of ASCT. Prior to ASCT, he received a conditioning regimen as set out above for patient No. 16. The ASCT consisted of bone marrow cells only ($0.64\times10^8$/kg). On day +110, the patient received $4\times10^7$ T cells/kg of PBL from an HLA-compatible sister. On the same day as the administration of the Allo-CMI treatment, the patient also received $6\times10^6$ IU of rhIL-2/$m^2$/day for 3 days, by subcutaneous injection. Prior to the Allo-CMI treatment, the patient received melphalan at 15 mg/$m^2$ with adequate hydration. On day +150, the patient received $3.3\times10^7$ ADL/kg from the HLA-matched donor. The ADL were produced by exposing the donor's PBL to 6,000 IU/ml rhIL-2 for four days in culture. On the same day as the administration of the Allo-CCI treatment, the patient also received $6\times10^6$ IU of rhIL-2/$m^2$/day for 3 days, by subcutaneous injection. Prior to the Allo-CCI treatment, the patient received melphalan at 30 mg/$m^2$.

Six (6) days following the Allo-CCI treatment, the patient developed bone marrow aplasia. An allogeneic bone marrow transplant was performed with the matched PBL donor's bone marrow cells ($3.52\times10^8$/kg), depleted of immunocompetent T cells using Campath-1G (0.1 $\mu$g/$10^6$ nucleated cells).

Patient No. 23

This male patient was diagnosed with NHL, Intermediate Grade, and was in first partial remission at the time of ASCT. He was 38 years old at the time of ASCT. Prior to ASCT, he received a conditioning regimen as set out above for patient No. 16. The ASCT consisted of bone marrow cells and peripheral blood stem cells combined. Following partial hematopoietic recovery, the patient received $2.8\times10^7$ T cells/kg of PBL from an HLA-compatible sibling. On the same day as the administration of the first Allo-CMI treatment, the patient also received $6\times10^6$ IU of rhIL-2/$m^2$/day for 3 days, by subcutaneous injection.

Notes on Patient No.'s 24–29

Patients 24–29 are breast cancer patients who were treated with a debulking regimen including ASCT. This was followed by Allo-CMI and, in some cases, Allo-CCI. Six patients with metastatic disease, with very grave prognoses, were offered immunotherapy according to the present invention. The advanced nature of the malignancies tempered expectations of complete disease eradication, but in the absence of viable therapeutic alternatives, the decision was made to proceed. Of the six patients, four were with evidence of major metastatic disease at the time immunotherapy was initiated. None of these patients showed evidence of engraftment. As such, the infused allogeneic cells may not have had sufficient time to mount a full GVT response. Even in mice, a residence time for the infused allogeneic cells of 2–3 weeks is required to obtain tumor elimination. Weiss et al., Effective Graft vs. Leukemia Effects Independently of Graft vs. Host Disease Following T-Cell depleted allogeneic bone marrow transplantation in a murine model of B-Cell Leukemia/Lymphoma (BCL1): Role of Cell Therapy and rHIL-2. J. Immunology 153(6): 2562–7 (Sept. 1994). Nevertheless, as described below, one of these patients showed a pronounced, though transient, response to cell therapy.

Two of the metastatic breast cancer patients entered the study in remission, after elimination of tumor bulk by chemotherapy prior to cell therapy. As described below, both of these patients show no evidence of disease over 11 and over 9 months following ASCT, are free of any symptoms, and have Karnofsky scores of 100%. This is in spite of the fact that, again, there was no evidence of engraftment. With future patients, engraftment will be possible with more aggressive application of the cell therapy.

Patient No. 24

This female patient was diagnosed with metastatic breast cancer, with metastases to the liver and spine. She underwent a right partial mastectomy with axillary lymph node dissection showing involvement of 18/35 lymph nodes. The patient was 43 years old at the time of ASCT. Prior to ASCT, she received a conditioning regimen of carboplatin, 200 mg/m$^2$/day, days −7 to −4; thiotepa, 60 mg/m$^2$/day, days −6 to −4; etoposide, 200 mg/m$^2$/day, days −5 to −3; and melphalan, 60 mg/m$^2$/day, days −4 to −3.

At the time of ASCT, the patient showed elevation of the breast cancer cell marker CA-15.3. ASCT consisted of 3.74×10$^8$ peripheral blood stem cells/kg, infused IV on day 0. The stem cells were collected after mobilization with G-CSF (7.5 mg/kg/day for 5 days) using three collections of the CS 3000® Plus blood cell separator. Following ASCT, the patient recovered with no complications and was discharged on day 20 post-ASCT.

A fully HLA-matched (A, B, DR and mixed lymphocyte reaction (MLR)-negative) sibling was chosen as donor of PBL for Allo-CMI. On day +77, when the patient had achieved a stable clinical condition (WBC: 2,700/mm$^3$; Hb: 9.1 g %; platelets: 56,000/mm$^3$), the patient received 3.2×10$^7$ T cells/kg of PBL from an HLA-matched sibling. Starting on the same day as the administration of the first Allo-CMI treatment, the patient also received 6×10$^6$ IU of rhIL-2/m$^2$/day for 3 days, by subcutaneous injection. On day +117, the patient received 5.4×10$^7$ T cells/kg of ADL, together with in vivo rhIL-2 as described above. ADL were produced as described above. On day +162, the patient received 1.11×10$^8$ T cells/kg of PBL (not ADL), together with in vivo rhIL-2 as described above. On day +165, the patient received 8.6×10$^7$ T cells/kg of ADL, together with in vivo rhIL-2 as described above. ADL were produced as described above. On day +343, the patient received 1.72×+10$^8$ T cells/kg of ADL (expanded in vitro with phytohaemagglutinin), together with in vivo rhIL-2 as described above.

Patient No. 25

This male patient was diagnosed with metastatic breast cancer, with metastases to the bone marrow, sternum and vertebrae T$_4$ to T$_7$. He underwent lumpectomy with axillary lymph node dissection showing involvement of 16/18 lymph nodes. The patient was 36 years old at the time of ASCT. Prior to ASCT, he received a conditioning regimen of carboplatin, 200 mg/m$^2$/day, days −7 to −4; thiotepa, 60 mg/m$^2$/day, days −6 to −4; etoposide, 200 mg/m$^2$/day, days −5 to −3; and melphalan, 60 mg/m$^2$/day, days −4 to −3.

ASCT consisted of 1.64×10$^8$ peripheral blood stem cells/kg, infused IV on day 0. The stem cells were collected after mobilization with G-CSF (7.5 mg/kg/day for 5 days) using three collections of the CS 3000® Plus blood cell separator. Following ASCT, the patient recovered with no complications and was discharged on day 20 post-ASCT.

A fully HLA-matched (A, B, DR and mixed lymphocyte reaction (MLR)-negative) brother was chose as donor of PBL for Allo-CMI. On day +33, as soon as the patient had achieved a stable clinical condition (WBC: 11,000/mm$^3$; Hb: 11.5 gt; platelets: 201,000/mm$^3$), the patient received 2.3×10$^7$ T cells/kg of PBL from an HLA-matched brother. Starting on the same day as the administration of the first Allo-CMI treatment, the patient also received 6×10$^6$ IU of rhIL-2/m$^2$/day for 3 days, by subcutaneous injection. On day +90, the patient received 9.4×10$^6$ ADL/kg from the same donor. The ADL were produced by exposing the donor's PBL to 6,000 IU/ml rhIL-2 for four days in culture. On the same day as the administration of the Allo-CCI treatment, the patient also received 6×10$^6$ IU of rhIL-2/m$^2$/day for 3 days, by subcutaneous injection. On day +170, the patient received 6.7×10$^7$ T cells/kg of PBL from the same donor. On the same day as the administration of the Allo-CCI treatment, the patient also received 6×10$^6$ IU of rhIL-2/m$^2$/day for 3 days, by subcutaneous injection.

Patient No. 26

This female patient was diagnosed with metastatic breast cancer, with involvement of 18/30 lymph nodes. The patient was 36 years old at the time of ASCT, with no evidence of disease. Prior to ASCT, she received a conditioning regimen of carboplatin, 200 mg/m$^2$/day, days −7 to −4; thiotepa, 60 mg/m$^2$/day, days −6 to −4; etoposide, 200 mg/m$^2$/day, days −5 to −3; and melphalan, 60 mg/m$^2$/day, days −4 to −3. ASCT consisted of 1.86×10$^8$ peripheral blood stem cells/kg, infused IV on day 0. The patient relapsed five (5) months after ASCT, with bone metastases.

On day +180, the patient received 4×10$^7$ T cells/kg of PBL from an HLA-compatible donor. Starting on the same day as the administration of the first Allo-CMI treatment, the patient also received 6×10$^6$ IU of rhIL-2/m$^2$/day for 3 days, by subcutaneous injection. On day +210, the patient received 1.11×10$^8$ T cells/kg of PBL from the same donor. On the same day as the administration of the second Allo-CMI treatment, the patient also received 6×10$^6$ IU of rhIL-2/m$^2$/day for 3 days, by subcutaneous injection. On day +216, the patient received 3.3×10$^7$ T cells/kg of ADL from the same donor, together with in vivo rhIL-2 as described above. The ADL were produced by exposing the donor's PBL to 6,000 IU/ml rhIL-2 for four days in culture.

Patient No. 27

This female patient was diagnosed with metastatic breast cancer, with involvement of 11/31 lymph nodes and metastases to the vertebrae. The patient was 44 years old at the time of ASCT, with elevation of a breast cancer cell marker, CA-15.3. Prior to ASCT, she received a conditioning regimen of carboplatin, 200 mg/m$^2$/day, days −7 to −4; thiotepa, 60 mg/m$^2$/day, days −6 to −4; etoposide, 200 mg/m$^2$/day, days −5 to −3; and melphalan, 60 mg/m$^2$/day, days −4 to −3. ASCT consisted of 2.79×10$^8$ peripheral blood stem cells/kg, infused IV on day 0.

On day +210, the patient received 2.98×10$^7$ T cells/kg of PBL from an HLA-compatible donor. Starting on the same day as the administration of the first Allo-CMI treatment, the patient also received 6×10$^6$ IU of rhIL-2/m$^2$/day for 3 days, by subcutaneous injection. On day +270, the patient received 6.54×10$^7$ ADL/kg from the same donor. The ADL were produced by exposing the donor's PBL to 6,000 IU/ml rhIL-2 for four days in culture. On the same day as the administration of the Allo-CCI treatment, the patient also received 6×10$^6$ IU of rhIL-2/m$^2$/day for 3 days, by subcutaneous injection.

Patient No. 28

This female patient was diagnosed with metastatic breast cancer, with metastases to the ribs and vertebrae. The patient was 54 years old at the time of ASCT. Prior to ASCT, she received a conditioning regimen of carboplatin, 200 mg/m$^2$/day, days −7 to −4; thiotepa, 60 mg/m$^2$/day, days −6 to −4; etoposide, 200 mg/m$^2$/day, days −5 to −3; and melphalan, 60 mg/m$^2$/day, days −4 to −3. ASCT consisted of 2.69×10$^8$ peripheral blood stem cells/kg, infused IV on day 0. The patient showed no evidence of disease at the time of initiation of Allo-CMI treatment.

On day +125, the patient received $3.3 \times 10^7$ T cells/kg of PBL from an HLA-compatible donor. Starting on the same day as the administration of the first Allo-CMI treatment, the patient also received $6 \times 10^6$ IU of rhIL-2/m$^2$/day for 3 days, by subcutaneous injection.

Patient No. 29

This female patient was diagnosed with metastatic breast cancer, with bone metastases as well as metastases to cervical and supraclavicular lymph nodes. The patient was 51 years old at the time of ASCT. Prior to ASCT, she received a conditioning regimen of carboplatin, 200 mg/m$^2$/day, days −7 to −4; thiotepa, 60 mg/m$^2$/day, days −6 to −4; etoposide, 200 mg/m$^2$/day, days −5 to −3; and melphalan, 60 mg/m$^2$/day, days −4 to −3. ASCT consisted of $1.71 \times 10^8$ peripheral blood stem cells/kg, infused IV on day 0. The patient showed no evidence of disease at the time of initiation of Allo-CMI treatment.

On day +160, the patient received $3.45 \times 10^7$ T cells/kg of PBL from an HLA-compatible donor. Starting on the same day as the administration of the first Allo-CMI treatment, the patient also received $6 \times 10^6$ IU of rhIL-2/m$^2$/day for 3 days, by subcutaneous injection. On day +211, the patient received $5 \times 10^7$ ADL/kg from the same donor. The ADL were produced by exposing the donor's PBL to 6,000 IU/ml rhIL-2 for four days in culture. On the same day as the administration of the Allo-CCI treatment, the patient also received $6 \times 10^6$ IU of rhIL-2/m$^2$/day for 3 days, by subcutaneous injection.

Portions of the above-described patient treatment protocols are summarized in Table 1, below. Patients are grouped according to disease (AML, CML, NHL and breast cancer).

TABLE 1[a]

| Patient No. | Status Pre-ASCT | Cond. Regimen | Type ASCT | Allo Cells (T Cells/Kg) |
|---|---|---|---|---|
| AML: | | | | |
| 1 | 1CR | BU/CY | ABMT: Purged | PBL $10^4$ - $10^7$ (day +1 to +47) |
| 2 | 1CR | BU/CY | ABMT: Purged | PBL $10^4$ - $10^7$ (day +1 to +80) |
| 3 | 1CR | BU/CY | ABMT: Non-Purged | PBL $10^7$ + IL2 (day +1) |
| 4 | 1CR | BU/CY + TT | ABMT: Non-Purged | PBL $10^7$ + IL2 (day +1) |
| 6 | 1CR | BU/CY + TT | ABMT: Non-Purged | 1. PBL<br>2. PBL + IL2 |
| 13 | 1CR | BU/CY + TT | ABMT: Non-Purged | 1. PBL |
| 14 | 2PR | BU/CY + MX | ABMT: Non-Purged | 1. PBL<br>2. Cytoxan/PBL + IL2 |
| 15 | 1CR | BU/CY + TT | ABMT: Non-Purged | 1. PBL<br>2. Cytoxan/PBL + IL2<br>3. Cytoxan/ADL + IL2 |
| CML: | | | | |
| 5 | C(Ph−) | CY/TBI | ABMT: Non-Purged | 1. PBL<br>2. PBL + IL2<br>3. ADL + IL2 |
| 7 | C(Ph+) | CY/TBI | ABMT: Non-Purged | 1. PBL<br>2. PBL + IL2 |
| NHL: | | | | |
| 8 | 2PR | ETACM | AMBT + PBSC: Purged | 1. PBL<br>2. PBL + IL2<br>3. Allogeneic BMT (due to marrow aplasia) |
| 9 | 2PR | ETACM | ABMT: Purged | 1. PBL<br>2. PBL + IL2<br>3. ADL + IL2 |
| 10 | 2CR | ETACM | ABMT + PBSC: Purged | 1. PBL<br>2. PBL + IL2<br>3. ADL + IL2 |
| 11 | 2CR | ETACM | ABMT + PBSC: Purged | 1. PBL<br>2. PBL<br>3. PBL<br>4. PBL + IL2 |
| 12 | Relapse | ETACM | ABMT: Non-Purged | 1. PBL<br>2. PBL + IL2 |
| 16 | 2PR | ETACM | ABMT + PBSC: Non-Purged | 1. PBL<br>2. Cytoxan/PBL + IL2<br>3. Melphalan/ADL + IL2 |
| 17 | 3PR | ETACM | ABMT: Non-Purged | 1. Cytoxan/PBL + IL2<br>2. Cytoxan/ADL + IL2 |
| 18 | 2CR | ETACM | ABMT + PBSC: Non-Purged | 1. Cytoxan/PBL + IL2<br>2. Melphalan/ADL + IL2<br>3. Allogeneic BMT (due to marrow aplasia) |
| 19 | Refractory | ETACM | ABMT + PBSC: Non-Purged | 1. PBL + IL2<br>2. Melphalan/ADL + IL2 |
| 20 | 2CR | ETACM | ABMT: Non-Purged | 1. Cytoxan/PBL + IL2<br>2. Allogeneic BMT (due |

TABLE 1a-continued

| Patient No. | Status Pre-ASCT | Cond. Regimen | Type ASCT | Allo Cells (T Cells/Kg) |
|---|---|---|---|---|
| 21 | 2PR | ETACM | ABMT + PBSC: Purged | to marrow aplasia)<br>1. Cytoxan/PBL + IL2 |
| 22 | 3CR | ETACM | ABMT: Non-Purged | 1. Melphalan/PBL + IL2<br>2. Melphalan/ADL + IL2<br>3. Allogeneic BMT (due to marrow aplasia) |
| 23 | 1PR | ETACM | ABMT + PBSC: Non-Purged | 1. PBL + IL2 |
| BREAST CANCER: | | | | |
| 24 | Metastatic | CTEM | PBSC: Non-Purged | 1. PBL + IL2<br>2. ADL + IL2<br>3. ADL + IL2<br>4. ADL + IL2 |
| 25 | Metastatic | CTEM | PBSC: Non-Purged | 1. PBL + IL2<br>2. ADL + IL2<br>3. ADL + IL2 |
| 26 | Metastatic | CTEM | PBSC: Non-Purged | 1. PBL + IL2<br>2. PBL + IL2<br>3. ADL + IL2 |
| 27 | Metastatic | CTEM | PBSC: Non-Purged | 1. PBL + IL2<br>2. ADL + IL2 |
| 28 | Metastatic (Remission) | CTEM | PBSC: Non-Purged | 1. PBL + IL2 |
| 29 | Metastatic (Remission) | CTEM | PBSC: Non-Purged | 1. PBL + IL2<br>2. ADL + IL2 | aTerms used in the Table are defined as follows:
1CR, 2CR: First or second complete remission, respectively.
1PR, 2PR, 3PR: First, second or third partial remission, respectively.
CP(Ph−): Chronic phase, no cytogenetic evidence of Philadelphia chromosome.
CP9Ph+): Chronic phase, cytogenetic evidence of presence of Philadelphia chromosome.
BU/CY: Conditioning regimen of Busulfan, 4 mg/kg, days 6 through 9 pre-ASCT (days −9 to −6), as well as Cytoxan (cyclophosphamide), 50 mg/kg, days −5 to −2, Cotrimoxazol, 10 mg/kg, days −10 to −2, Allopurinol, 300 mg/kg, days −10 to −1 and cytosine arabinoside (Ara-C), 25 mg intrathecally.
BU/CY + TT: Conditioning regimen of Busulfan 4 mg/kg, days −9 to −6, Cytoxan 60 mg/kg, days −3 to −2, Thiotepa 5 mg/kg/day, days −5 to −4; Cotrimoxazol, 10 mg/kg, days −10 to −2, Allopurinol, 300 mg/kg, days −10 to −1 and Ara-C, 25 mg intrathecally.
BU/CY + MX: Conditioning regimen of Busulfan 4 mg/kg, days −9 to −6; Cytoxan 60 mg/kg, days −3 to −2; Mitoxantrone 6 mg/m$^2$/day, days −5 to −4; Cotrimoxazol, 10 mg/kg, days −10 to −2, Allopurinol, 300 mg/kg, days −10 to −1 and Ara-C, 25 mg intrathecaly.
CY/TBI: Conditioning regimen of total body irradiation (TBI) 200 cGY/day, days −5 to −3, and Cytoxan 60 mg/kg, days −2 to −1.
ETACM: Conditioning regimen of etoposide, 200 mg/m$^2$/day, days −6 to −3; thiotepa, 40 mg/m$^2$/day, days −5 to −2; Ara-C, 200 mg/m$^2$/day, days −4 to −1; Cytoxan, 60 mg/kg/day −3; and melphalan, 60 mg/m$^2$/day, days −2 to −1.
CTEM: Conditioning regimen of carboplatin, 200 mg/m$^2$/day, days −7 to −4; thiotepa, 60 mg/m$^2$/day, days −6 to −4; etoposide, 200 mg/m$^2$/day, days −5 to −3; and melphalan, 60 mg/m$^2$/day, days −4 to −3.
ABMT: Infusion of stem cells extracted directly from the bone marrow.
PBSC: Infusion of stem cells taken from peripheral blood following mobilization from the bone marrow.
PBL, ADL: Without further numerical designation, PBL (peripheral blood lymphocytes) and ADL (Activated donor lymphocytes) refer to one infusion of $\geq 10^7$ cells/kg of patient body weight. For patient No.'s 5–18, the first infusion of allogeneic cells was done only after attainment of partial hematopoiesis reconstitution.
Cytoxan/PBL or ADL: Cyclophosphamide (Cytoxan) administered prior to infusion of $\geq 10^7$ cells/kg of PBL or ADL.
Melphalan/PBL or ADL: Melphalan administered prior to infusion of $\geq 10^7$ cells/kg of PBL or ADL.

II. RESULTS

The above-described patients have been followed for various lengths of time. The disease status of the patients is summarized below:

Patient No. 1 relapsed after 6 months and died at 9 months after ASCT.

Patient No. 2 relapsed after 12 months and died at 20 months after ASCT.

Patient No. 3 relapsed after 36 months. After receiving an allogeneic bone marrow transplant, the patient went into a complete remission, but died of GVHD 6 weeks after the allogeneic BMT.

Patient No. 4 is alive and well 36 months after ASCT, with a Karnofsky score of 100%.

Patient No. 5 is alive and hematologically in complete remission with no chemotherapy requirement and Karnofsky score of 100%, over 34 months after ASCT. PCR for the bcr/abl translocation characteristic of the Philadelphia chromosome fluctuates between negative and positive, although the patient's disease appears fully controlled. The patient is receiving 9×10$^6$ units of IFNα (Roferon A, S.C.) every day.

Patient No. 6 is alive and well over 35 months after ASCT with no evidence of disease and Karnofsky score of 100%.

Patient No. 7 is alive and hematologically in complete remission with no chemotherapy requirement and Karnofsky score of 100%, over 33 months post-ASCT. Currently, the patient is on IFNα treatment. PCR for the bcr/abl translocation characteristic of the Philadelphia chromosome fluctuates between negative and positive, although the patient's disease appears fully controlled.

Patient No. 8 is alive and well over 36 months after initial ASCT and over two years following allogeneic BMT, with no evidence of lymphoma. The patient has mild cutaneous chronic GVHD with Karnofsky score of 100%.

Patient No. 9 relapsed after 18 months post-ASCT. The patient is being treated with Allo-CMI/CCI from another HLA-matched donor.

Patient No. 10 is alive and well over 29 months after ASCT with no evidence of disease.

Patient No. 11 is alive and well over 28 months after ASCT with no evidence of disease.

Patient No. 12 underwent relapse at 3 months post-ASCT and died at 5 months post-ASCT.

Patient No. 13 underwent relapse at 4 months post-ASCT. He did not have a chance to receive allo-CMI with rhIL2 due to severe unrelated pulmonary complications. The patient died 5 months after relapse.

Patient No. 14 is alive and well with no evidence of disease over 13 months post-ASCT, with Karnofsky score of 100%. PCR analysis of blood shows no evidence of RAR-alpha, the typical molecular marker for AML.

Patient No. 15 is alive and well with no evidence of disease over 15 months post-ASCT, with Karnofsky score of 100%.

Patient No. 16 relapsed after 7 months post-ASCT. The patient is alive and clinically well with evidence of disease at 14 months post-ASCT. He was not referred for further treatment and is being treated by his referring physician.

Patient No. 17 is alive and well with no evidence of disease over 15 months post-ASCT.

Patient No. 18 is alive and well with no evidence of disease over 14 months post-ASCT.

Patient No. 19 is alive and well with no evidence of disease over 13 months post-ASCT.

Patient No. 20 died of multi-organ failure 13 days following allogeneic BMT for marrow aplasia.

Patient No. 21 is alive and well with no evidence of disease over 9 months post-ASCT.

Patient No. 22 died of pneumonia and Candida sepsis 9 days following allogeneic BMT for marrow aplasia.

Patient No. 23 relapsed at 5 months post-ASCT. He is being treated with radiation therapy to involved areas and will be treated with immunotherapy as soon as the radiation treatments are over.

Figure 5A:
FIG. 5 shows photographs of computerized tomography (CT) scans of a breast cancer patient. Panel A shows the presence of breast cancer metastases (arrows) in the liver before Allo-CMI/CCI. The CT image in Panel B fails to reveal liver metastases in the same patient after being given an Allo-CMI/CCI regimen.
Figure 5B:
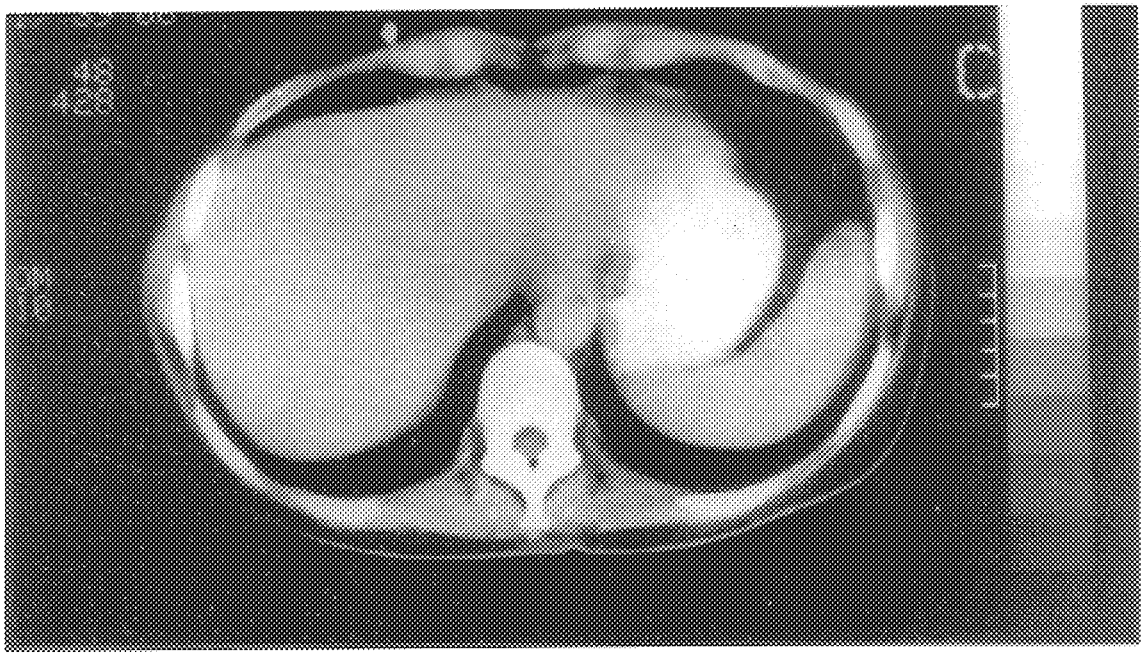

Patient No. 24 showed a marked partial remission of 3 months duration, during which time there was a distinctive disappearance of liver metastases from CT scan images (see FIG. 5), and there was a marked decline in the level of the breast cancer cell marker 15.3 (118 down to less than 4). The patient has relapsed and is now in a state of disease progression.

Patient No. 25 has progressive disease.

Patient No. 26 has progressive disease.

Patient No. 27 has progressive disease.

Patient No. 28 is alive and well with no evidence of disease over 11 months post-ASCT.

Patient No. 29 is alive and well with no evidence of disease over 9 months post-ASCT.

The results reported above indicate that Allo-CMI and Allo-CCI may be the most rational and practical approached for eradication of residual malignant cells. GVT effects induced by administration of allogeneic lymphocytes may be further enhanced by administration in vivo of rhIL2.

EXAMPLE 3

Utility of Cytokines Other Than IL2

Cytokines used in the following experiments were obtained as follows: (1) rhIL2 was provided by Dr. C. R. Franks (EuroCetus BY, Amsterdam, The Netherlands) as a lyophilized powder in 1 mg vials containing $18 \times 10^6$ international units (IU). (2) Recombinant interferon-gamma (rIFNγ) was provided by Roussel Uclaf (Romainville, France) as a lyophilized powder containing $2 \times 10^7$ U/mg. (3) Recombinant human IL-6 (rIL-6) was kindly provided by Dr. M. Revel and Dr. O. Laub (InterPharm Laboratories, Rehovot., Israel) in a concentration of 1.13 mg/ml protein containing $43 \times 10^6$ IU/ml. (4) Recombinant human IL-7 (rhIL-7) was provided by Pepro Tech (New Jersey, USA) as lyophilized powder and was reconstituted to 100 mg/ml.

Lymphocytes were preactivated in vitro with rhIL2 or with combinations of rhIL2 and other cytokines for four days at 37° C. Concentrations of cytokines used for in vitro incubation of lymphocytes were as follows: (a) rhIL2: 6000 IU/ml; (b) rIL6: 100–1000 U/ml; (c) rIL7: long/ml; and (d) IFNγ: 1000 U/ml. Anti-tumor effects of ADL collected post-culturing were assayed against natural killer (NK)-sensitive K562 tumor cells and NK-resistant Daudi tumor cells. The in vitro toxicity was evaluated by specific chromium release following incubation of effector cells with chromium-labeled tumor cells. Results are presented below as lytic units per $10^6$ effector cells, determined for 30% lysis of $5 \times 10^3$ target cells:

|  | Cytotoxicity (Lytic Units/$10^6$ Cells) | |
| --- | --- | --- |
|  | Anti-Daudi | Anti-K562 |
| IL2 alone | 48 | 53 |
| IL2 + IL6 + IL7 + IFN | 210 | 129 |

EXAMPLE 4

Selected CD8+T Lymphocytes as Agents of the Graft-Versus-Tumor Effect

Mice were purchased and maintained as described in EXAMPLE 1. Use and maintenance of BCL1 leukemia cells were as described in EXAMPLE 1. rhIL-2 was obtained from EuroCetus (Amsterdam, Holland). Concentrations of rhIL-2 are expressed in International Units (IU), where 6,000 IU is equivalent to 1,000 Cetus Units.

In a first set of experiments, BALB/c x C57BL/6 F1(F1) recipients were inoculated with $10^5$ BCL1 leukemia cells. BCL1 cells are of BALB/c origin. The recipient mice were conditioned with total body irradiation (TBI) at 750 cGY; 24 hours later the conditioned mice received Allo-CMI treatment using $15 \times 10^6$ spleen cells obtained from C57BL/6 (experimental) or F1 (control) donors. The spleen cells used for Allo-CMI were either untreated or treated with specific monoclonal antibodies to eliminate well-defined T-cell subsets (CD4 or CD8). CD4+ cells were eliminated with the YTS 191 antibody, and CD8+ cells were eliminated with the YTS 169 antibody. Both antibodies are IgG2b and, as such, bind effectively to the recipient host Fc-positive reticuloendothelial system, resulting in cell lysis through antibody-dependent cell-mediated cytotoxicity (ADCC). The antibodies were provided by Drs. Steve Cobbold and Herman Waldman, Cambridge University, United Kingdom.

In order to assess the effect of Allo-CMI on elimination of tumor cells in the recipient host, $10^5$ spleen cells from treated recipients at 49 days following Allo-CMI were adoptively transferred to secondary BALB/c recipients. Leukemia was followed in secondary recipients in order to assess whether or not spleen cells obtained from the treated animals contained clonogenic tumor cells.

Figure 6:
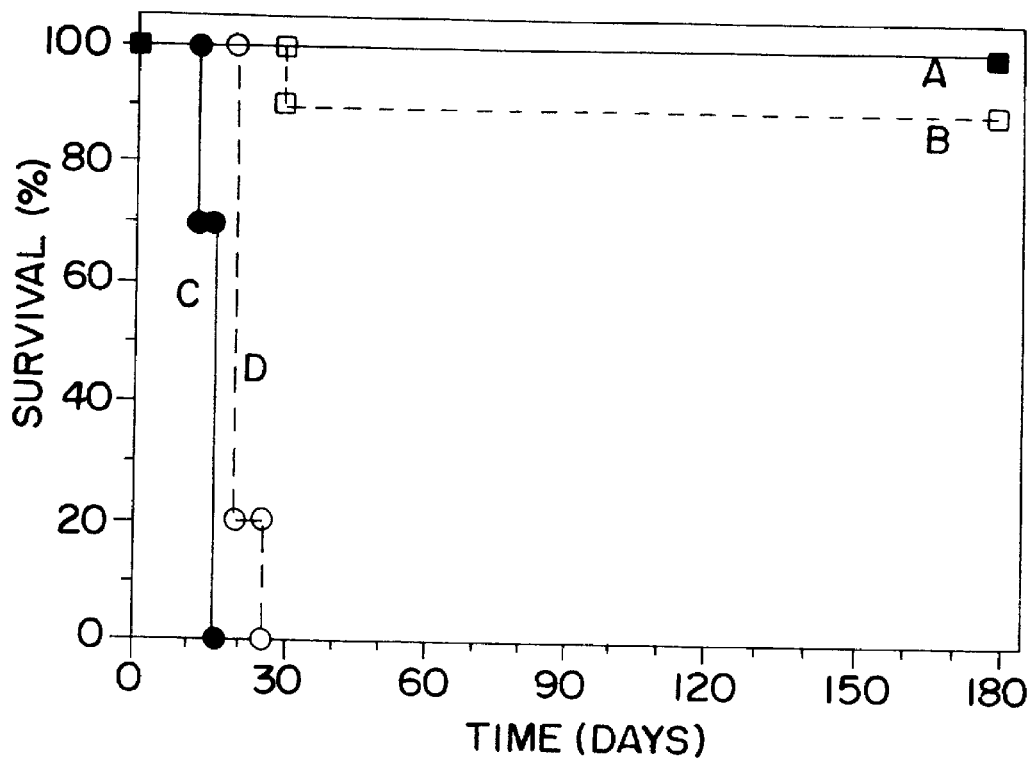
FIG. 6 depicts the results of adoptive transfer of spleen cells obtained from irradiated F1 mice inoculated with $10^5$ BCL1 cells. The irradiated mice received unselected allogeneic T cells or T-cell populations selected for CD4+ or CD8+ cells; control mice received syngeneic (F1) T lymphocytes. A =unselected C57 spleen cells; B =CD8+ cells, i.e., spleen cells treated with an antibody that depletes the cell population of CD4+ cells; C =CD4+ cells, i.e., spleen cells treated with an antibody that depletes the cell population of CD8+ cells; D=unselected control (F1) spleen cells.

Results are shown in FIG. 6. The graph is a composite of two experiments in which 9/10 and 8/10, respectively of recipients treated with CD4-depleted spleen cells remained disease free, whereas 0/7 and 0/10 recipients treated with CD8-depleted spleen cells remained disease free. The data indicate that CD8+ cells, but not CD4+ cells, were capable of eliciting a GVT response in the recipient mice.

In a second set of experiments, T-cell subsets were again evaluated, this time as ADL administered in concert with in vivo administration of rhIL2. F1 recipients were inoculated with $10^5$ BCL1 leukemia cells. Recipients were conditioned with TBI at 750 cGY. On the following day each recipient received $10 \times 10^6$ activated donor lymphocytes (ADL). The ADL (spleen cells activated in vitro with rhIL2 at 6,000 IU/ml for 4 days) were given untreated or pretreated with the anti-CD4 and anti-CD8 antibodies described above to deplete the cell populations of well-defined T-cell subsets. In order to amplify the potential anti-tumor effects in vivo and to investigate whether or not lack of well-defined T-cell subsets may be compensated for by in vivo treatment with rhIL-2, recipients were administered 120,000 IU rhIL-2 intraperitoneally twice a day for five days.

In order to assess the effect of Allo-CMI on elimination of tumor cells in the recipient host, $10^5$ spleen cells from treated recipients at 12 days following Allo-CMI were adoptively transferred to secondary BALB/c recipients. Leukemia was followed in secondary recipients in order to assess whether or not spleen cells obtained from the treated animals contained clonogenic tumor cells.

Figure 7:
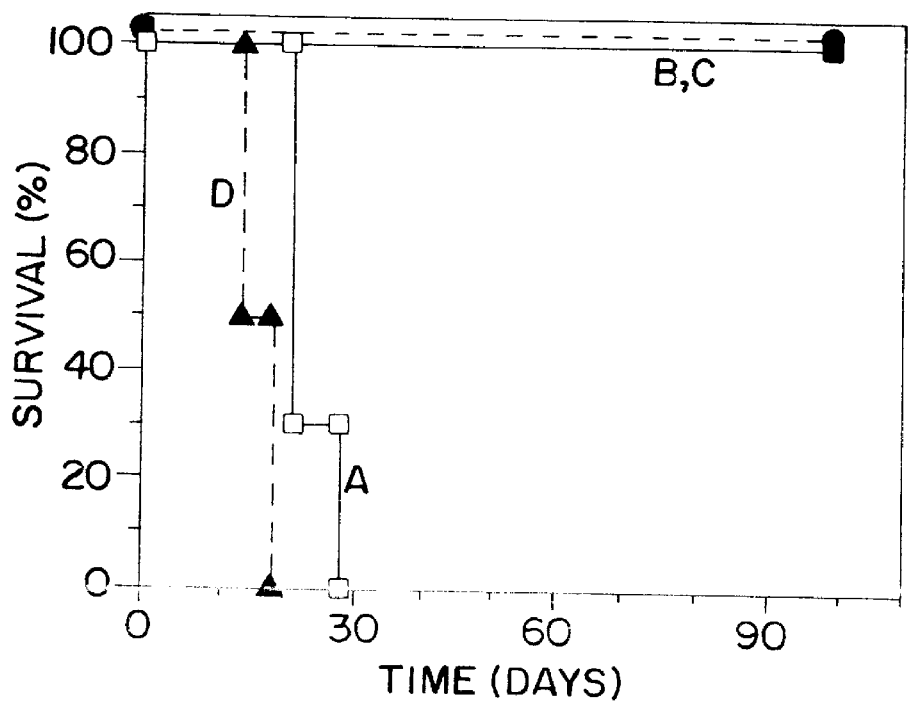
FIG. 7 depicts the results of adoptive transfer of spleen cells obtained from irradiated F1 mice inoculated with $10^5$ BCL1 cells. The irradiated mice received unselected allogeneic T cells or T-cell populations selected for CD4+ or CD8+ cells; control mice received syngeneic (F1) T lymphocytes. The cells were administered as ADL in concert with in vivo administration of rIL2. A =unselected C57 ADL administered without concomitant in vivo rIL2; B=unselected C57 ADL plus in vivo rIL2; C=CD8+ ADL, i.e., ADL treated with an antibody that depletes the cell population of CD4+ cells, plus in vivo rIL2; D=CD4+ ADL, i.e., ADL treated with an antibody that depletes the cell population of CD8+ cells, plus in vivo rIL2.

Results are shown in FIG. 7, which summarizes three separate experiments. The data demonstrate that rhIL-2 can enhance and restore full GVT activity to ADL even if CD4 cells are depleted. As such, rhIL-2 can substitute for CD4 cells under these conditions. In contrast, CD8-depleted ADL cannot be restored to full GVT activity by additional treatment i vivo with rhIL-2. These data confirm that the anti-leukemia effects are mediated by CD8+ T cells and further indicate that such effects can be enhanced by in vivo treatment with rhIL-2.

What is claimed is:

1. A method of treating a human cancer patient having malignant breast cancer cells, said patient having undergone a malignant cell debulking procedure and having further undergone autologous stem cell transplantation incident to said debulking procedure, said patient being at risk for disease relapse due to a population of residual malignant breast cancer cells that may remain viable in said patient following said debulking procedure, comprising:
   a) monitoring said patient until said patient is partially hematopoiesis recovered but is not fully immune-reconstituted;
   b) administering to said patient allogeneic lymphocytes in a regimen that causes a clinically significant graft-versus-malignant cell response; and
   c) monitoring said patient for levels of malignant breast cancer cells.

2. The method of claim 1, wherein said lymphocytes are HLA-compatible with said patient.

3. The method of claim 2, wherein said regimen comprises the following steps in sequence:
   a) treating said patient by administration of about $10^7$ cells/kg to about $10^9$ cells/kg of HLA-compatible, allogeneic lymphocytes;
   b) monitoring said patient for indications of a graft-versus-malignant cell response; and
   c) if no or insufficient graft-versus-malignant cell response develops in said patient, escalating said treatment by performing at least one procedure selected from the group consisting of (1) administration of a number of HLA-compatible, allogeneic lymphocytes greater than the number of lymphocytes administered in step (a); (2) administration of a number of HLA-compatible, allogeneic lymphocytes at least as great as the number of lymphocytes administered in step (a), accompanied by in vivo administration of at least one T-cell activator to said patient; (3) administration of HLA-compatible, allogeneic ADL to said patient; and (4) administration of HLA-compatible, allogeneic ADL, accompanied by in vivo administration of at least one T-cell activator to said patient;
   wherein more than one of said procedures is performed if no or insufficient graft-versus-malignant cell response develops in said patient following said first or subsequent procedure.

4. The method of claim 3, wherein step (a) of said regimen further comprises in vivo administration of at least one T-cell activator to said patient.

5. The method of claim 3, wherein said T-cell activator comprises at least one T-cell signal transduction pathway activator.

6. The method of claim 5, wherein said T-cell signal transduction pathway activator is selected from the group consisting of IL1, IL2, IL4, IL5, IL6, IL7, IL12, IL13, IFNα, IFNγ, TNFα, anti-CD3, anti-CD28, phytohemagglutinin, concanavalin-A, and phorbol esters.

7. The method of claim 1 wherein said breast cancer cells are metastatic breast cancer cells.

8. A method of treating a human cancer patient having malignant breast cancer cells, said patient having undergone a malignant cell debulking procedure and having further undergone autologous stem cell transplantation incident to said debulking procedure, said patient being at risk for disease relapse due to a population of residual malignant breast cancer cells that may remain viable in said patient following said debulking procedure, comprising:
   a) monitoring said patient until said patient is partially hematopoiesis recovered but is not fully immune-reconstituted;
   b) administering to said patient allogeneic lymphocytes in a regimen that causes a mild graft-versus-host response; and
   c) monitoring said patient for levels of malignant breast cancer cells.

9. The method of claim 8 wherein said breast cancer cells are metastatic breast cancer cells.

10. The method of claim 8, wherein said lymphocytes are HLA-compatible with said patient.

11. The method of claim 10, wherein said regimen comprises the following steps in sequence:
   a) treating said patient by administration of about $10^7$ cells/kg to about $10^9$ cells/kg of HLA-compatible, allogeneic lymphocytes;
   b) monitoring said patient for indications of a mild graft-versus-host response; and
   c) if no or insufficient graft-versus-host response develops in said patient, escalating said treatment by performing at least one procedure selected from the group consisting of (1) administration of a number of HLA-compatible, allogeneic lymphocytes greater than the number of lymphocytes administered in step (a); (2) administration of a number of HLA-compatible, allogeneic lymphocytes at least as great as the number of lymphocytes administered in step (a), accompanied by in vivo administration of at least one T-cell activator to said patient; (3) administration of HLA-compatible, allogeneic ADL to said patient; and (4) administration of HLA-compatible, allogeneic ADL, accompanied by in vivo administration of at least one T-cell activator to said patient;
   wherein more than one of said procedures is performed if no or insufficient graft-versus-malignant cell response develops in said patient following said first or subsequent procedure.

12. The method of claim 11, wherein step (a) of said regimen further comprises in vivo administration of at least one T-cell activator to said patient.

13. The method of claim 8, wherein said regimen comprises the following steps in sequence:
   a) administering to said patient about $10^7$ cells/kg to about $10^9$ cells/kg of HLA-compatible, allogeneic lymphocytes and at least one T-cell activator to said patient;
   b) monitoring said patient for signs of mild graft-versus-host response;
   c) if no or insufficient graft-versus-host response develops in said patient, administering about $10^7$ cells/kg to about $10^9$ cells/kg of HLA-compatible, allogeneic ADL and at least one T-cell activator to said patient; and
   d) monitoring said patient for signs of a mild graft-versus-host response.

14. The method of claim 8, wherein said regimen comprises the following steps in sequence:
   a) administering to said patient about $10^5$ cells/kg to about $10^9$ cells/kg of HLA-compatible, allogeneic lymphocytes comprising ADL, and at least one T-cell activator to said patient;
   b) monitoring said patient for signs of mild graft-versus-host response;
   c) if no or insufficient graft-versus-host response develops in said patient, administering about $10^5$ cells/kg to about $10^9$ cells/kg of HLA-compatible, allogeneic ADL and at least one T-cell activator to said patient; and
   d) monitoring said patient for signs of a mild graft-versus-host response.

15. The method of claim 11, wherein said T-cell activator comprises at least one T-cell signal transduction pathway activator.

16. The method of claim 15, wherein said T-cell signal transduction pathway activator is selected from the group consisting of IL1, IL2, IL4, IL5, IL6, IL7, IL12, IL13, IFNα, IFNγ, TNFα, anti-CD3, anti-CD28, phytohemagglutinin, concanavalin-A, and phorbol esters.

17. The method of claim 13, wherein said T-cell activator comprises at least one T-cell signal transduction pathway activator.

18. The method of claim 14, wherein said T-cell activator comprises at least one T-cell signal transduction pathway activator.

19. The method of claim 1, wherein said allogeneic lymphocytes are selected to have a substantially diminished graft-versus-host activity compared to unselected lymphocytes.

20. The method of claim 21, wherein said selected lymphocytes are CD8+ lymphocytes.

21. The method of claim 19, wherein said selected lymphocytes are HLA-mismatched with said patient.

22. The method of claim 19 wherein said breast cancer cells are metastatic breast cancer cells.

* * * * *